United States Patent [19]

Guindon et al.

[11] Patent Number: 5,081,145
[45] Date of Patent: Jan. 14, 1992

[54] INDOLE-2-ALKANOIC ACIDS COMPOSITIONS OF AND ANTI ALLERGIC USE THEREOF

[75] Inventors: Yvan Guindon; John W. Gillard, both of Quebec; Christiane Yoakim, Montreal; Thomas R. Jones, Kirkland; Rejean Fortin, Montreal-Nord, all of Canada

[73] Assignee: Merck Frosst Canada, Inc., Kirkland, Canada

[21] Appl. No.: 473,551

[22] Filed: Feb. 1, 1990

[51] Int. Cl.$^5$ ................. C07D 209/12; A61K 31/405
[52] U.S. Cl. .................... 514/419; 548/492; 548/494
[58] Field of Search .................. 548/494; 514/419

[56]  References Cited

U.S. PATENT DOCUMENTS

| 3,196,162 | 7/1965 | Sarett et al. | 260/319 |
| 3,242,162 | 3/1966 | Sarett et al. | 260/211 |
| 3,242,163 | 3/1966 | Sarett et al. | 260/211 |
| 3,242,193 | 3/1966 | Sarett et al. | 260/319 |
| 4,739,073 | 4/1988 | Kathawala | 548/414 X |

FOREIGN PATENT DOCUMENTS

| 50957 | 5/1982 | European Pat. Off. . |
| 454858 | 6/1968 | Switzerland . |
| 455777 | 7/1968 | Switzerland . |
| 948460 | 9/1960 | United Kingdom . |

OTHER PUBLICATIONS

Walton, et al., J. Med. Chem., 8, 204 (1965).
E. Walton, et al., J. Med. Chem., 11, 1252 (1968).

*Primary Examiner*—David B. Springer
*Attorney, Agent, or Firm*—Gabriel Lopez; Joseph F. DiPrima

[57]  ABSTRACT

Indole-2-alkanoic acids are disclosed. The compounds act as prostaglandin and thromboxane antagonists and are useful in treating asthma, inflammation, diarrhea, hypertension, angina, platelet aggregation, cerebral spasm, premature labor, spontaneous abortion and dismenorrhea and as cytoprotective agents.

6 Claims, No Drawings

INDOLE-2-ALKANOIC ACIDS COMPOSITIONS OF AND ANTI ALLERGIC USE THEREOF

CROSS-REFERENCE

This is a continuation of application Ser. No. 197,117 filed Jan. 21, 1988 which is a continuation-in-part of patent application U.S.S.N. 624,173, filed June 25, 1984, pending, both abandoned.

SUMMARY OF THE INVENTION

This invention relates to prostaglandin antagonists useful in treating a variety of conditions, such as allergic asthma where excessive contractile activity of prostaglandins and prostaglandin biosynthetic intermediates occur.

These compounds antagonize the actions of contractile prostaglandins, such as $PGF_{2\alpha}$, $PGG_2$, $PGH_2$, $PGD_2$, and $TXA_2$. The use of agents which act as prostaglandin antagonists offers new approaches to therapy in a number of disease states. For example, certain prostaglandins, such as $PGF_{2\alpha}$, $PGD_2$, $PGG_2$, and $PGH_2$, are potent contractants of bronchial muscle. Indeed human asthmatics have been shown to be especially sensitive to the bronchial constricting action of $PGF_{2\alpha}$.

The compounds of the present invention also produce antithrombotic effects. Thus, they are useful in the treatment and/or prevention of thromboembolic diseases such as arterial thrombosis.

In addition to the involvement of contractile prostaglandins in chronic obstructive lung disease (or asthma), prostaglandins are known to play a role in other allergic conditions, as well as inflammation, diarrhea, hypertension, angina, platelet aggregation, cerebral spasm, cerebral ischemia, myocardial ischemia, premature labor, spontaneous abortion, dismenorrhea, glomerular nephritis, and systemic lupus erythematosis. Consequently, the compounds of this invention will alleviate the above mentioned diseases.

In addition to the prostaglandin antagonist actions, the compounds of this invention are inhibitors of the synthesis of leukotrienes. Leukotrienes $B_4$, $C_4$, $D_4$ and $E_4$ are known to contribute to various disease conditions such as asthma, psoriasis, inflammation, pain, ulcers and systemic anaphylaxis. Thus inhibition of the synthesis of such compounds will alleviate these disease states.

The compounds of the present invention may be used to treat or prevent mammalian (especially, human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The present invention relates to a pharmaceutical composition comprising a compound of the Formula I:

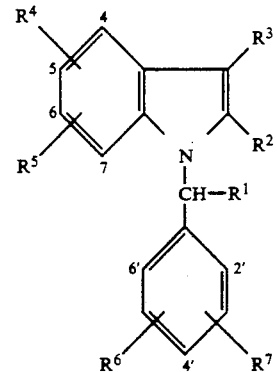

wherein:
$R^1$ is H or alkyl of 1 to 6 carbons or $R^1$ and $R^8$ taken together form a group $(CH_2)_v$ wherein v is 1 to 7;
$R^2$ is

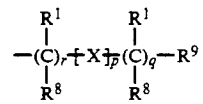

wherein:
each $R^8$ is independently H, OH, $C_1$ to $C_4$—O—alkyl or alkyl of 1 to 4 carbons; or an $R^1$ and an $R^8$ taken together form a group $(CH_2)_v$ wherein v is 1 to 7.
$R^9$ is $COOR^1$; $CH_2OH$; CHO; tetrazole; $NHSO_2R^{10}$ wherein $R^{10}$ is OH, alkyl or alkoxy of 1 to 6 carbons, perhaloalkyl of 1 to 6 carbons, phenyl or phenyl substituted by alkyl or alkoxy groups of 1 to 3 carbons, halogen, hydroxy, COOH, CN, formyl or acyl to 1 to 6 carbons; $CONHSO_2R^{10}$; hydroxymethylketone; CN; or $CON(R^8)_2$;
X is O; S; SO; $SO_2$; $NR^{11}$ wherein $R^{11}$ is H, alkyl of 1 to 6 carbons, acyl of 1 to 6 carbons, CN; $CR^1R^8$; or the unit

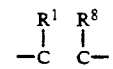

wherein the dotted line represents an optional triple bond and in which the $R^1$ and $R^8$ substituents are absent when a triple bond is present;
r and q are each independently 0 to 5 and p is 0 or 1 provided that the total of p, q and r is 2 to 6;
$R^3$ is H, alkyl of 1 to 6 carbons; phenyl or phenyl substituted by $R^4$; or $C_1$ to $C_4$ alkylphenyl or $C_1$ to $C_4$ alkylphenyl in which the phenyl is substituted by $R^4$;
$R^4$, $R^5$, $R^6$ and $R^7$ are each independently selected from:
  (1) hydrogen;
  (2) alkyl having 1 to 6 carbon atoms;
  (3) alkenyl having 2 to 6 carbon atoms;
  (4) —$(CH_2)_nM$ wherein n is 0 to 3 and M is
    a) $OR^{12}$;
    b) halogen;
    c) $CF_3$;
    d) $SR^{12}$;
    e) phenyl or substituted phenyl wherein substituted phenyl is as defined below in the definition of $R^{12}$;
    f) $COOR^{13}$;

g) 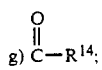

h) tetrazole;

i) 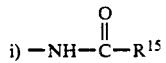

wherein $R^{15}$ is $C_1$ to $C_6$ alkyl, benzyl or phenyl;

j) $-NR^{13}R^{13}$;

k) $-NHSO_2R^{16}$ wherein $R^{16}$ is $C_1$ to $C_6$ alkyl, phenyl, or $CF_3$;

l) 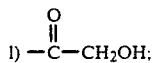

m) $-SOR^{12}$;

n) $-CONR^{13}R^{13}$;

o) $-SO_2NR^{13}R^{13}$;

p) $-SO_2R^{12}$;

q) $NO_2$;

r) 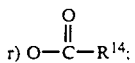

s) 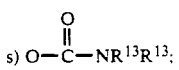

t) 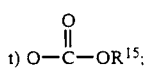

u) CN;

each $R^{12}$ independently is H; $C_1$ to $C_6$ alkyl; benzyl; phenyl or substituted phenyl wherein the substituents are $C_1$ to $C_3$ alkyl, halogen, CN, $CF_3$, $COOR^{13}$, $CH_2COOR^{13}$, $C_1$ to $C_3$ alkoxy, or $C_1$ to $C_4$ perfluoroalkyl;

each $R^{13}$ is independently H, phenyl or $C_1$ to $C_6$ alkyl; and each $R^{14}$ independently is H, $(CH_2)_nCOOR^{13}$ wherein n is 0 to 4, $C_1$ to $C_6$ alkyl, $CF_3$, phenyl, or substituted phenyl wherein substituted phenyl is as defined above in the definition of $R^{12}$; or a pharmaceutically acceptable salt thereof, and a pharmaceutically acceptable carrier.

As used herein, the terms "each independently" or the equivalents thereof are employed to describe a number of possible position isomers and/or structural variations. For example, as described above, $R^2$ is:

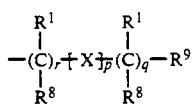

The letters r and q, represent possible alkane chains of from 0 to 5 carbon atoms, each having the $R^1$ and $R^8$ substituent groups. On each carbon atom of the alkane chain, the $R^1$ and/or $R^8$ substituent may be different. The above description therefore contemplates structures such as the following for the segments $-(CR^1R^8)_r-$ and $-(CR^1R^8)_q-$:

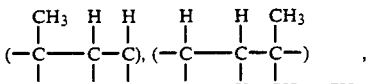

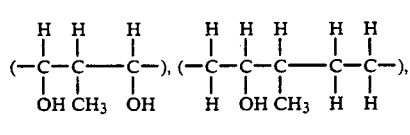

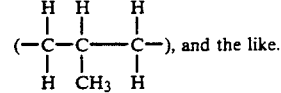

, and the like.

The alkyl groups referred to above may be straight chain or branched or may include cycloalkyl groups. As used herein, the term "lower" as applied to alkyl, acyl, alkoxy and the like, unless stated otherwise refers to groups having 1 to 6 carbon atoms. Halogen or halo means fluoro, chloro, bromo and/or iodo.

Pharmaceutically acceptable salts of the compounds described herein are included within the scope of the present invention. Such salts may be prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the potassium, sodium calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, tri-methylamine, diethanolamine, diethylamine, triethylamine, tripropylamine, ethanolamine, 2-dimethylaminoethanol, 2-diethylaminoethanol, tomethamine, lysine, arginine, histidine, caffeine, procaine, hydrabamine, choline, imidazole, betaine, ethylenediamine, glucosamine, methylglucamine, theobromine, purines piperazine, N,N-dibenzylethylenediamine, piperidine, N-ethylpiperidine, morpholine, N-ethylmorpholine, polyamine resins and the like.

Preferred compositions of the present invention comprise compounds of the Formula I wherein:

each $R^1$ is H or alkyl of 1 to 6 carbons or $R^1$ and $R^8$ taken together form a group $(CH_2)_v$ wherein v is 1 to 7; $R^2$ is

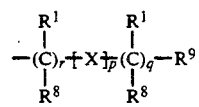

wherein:

each $R^8$ is independently H, OH, $C_1$ to $C_4$—O—alkyl or alkyl of 1 to 4 carbons; or an $R^1$ and an $R^8$ taken together form a group $(CH_2)_v$ wherein v is 1 to 7;

$R^9$ is $COOR^1$; $CH_2OH$; CHO; tetrazole; $CONHSO_2R^{10}$ wherein $R^{10}$ is OH, alkyl or alkoxy of 1 to 6 carbons, perhaloalkyl of 1 to 6 carbons, phenyl or phenyl substituted by alkyl or alkoxy groups of 1 to 3 carbons, halogen, hydroxy, COOH, CN, formyl or acyl to 1 to 6 carbons; hydroxymethylketone; CN; or $CON(R^8)_2$;

X is O; S; SO; SO$_2$; NR$^{11}$ wherein R$^{11}$ is H, alkyl of 1 to 6 carbons, acyl of 1 to 6 carbons, CN; CR$^1$R$^8$; or the unit

wherein the dotted line represents an optional triple bond and in which the R$^1$ and R$^8$ substituents are absent when a triple bond is present;

r and q are each independently 0 to 5 and p is 0 or 1 provided that the total of P, q and r is 2 to 4;

R$^3$ is H, alkyl of 1 to 6 carbons; phenyl or phenyl substituted by R$^4$; or C$_1$ to C$_4$ alkylphenyl or C$_1$ to C$_4$ alkylphenyl in which the phenyl is substituted by R$^4$;

R$^4$, R$^5$, R$^6$ and R$^7$ are each independently selected from:
(1) hydrogen;
(2) alkyl having 1 to 6 carbon atoms;
(3) alkenyl having 2 to 6 carbon atoms;
(4) —(CH$_2$)$_n$M wherein n is 0 or 1 and M is
 a) OR$^{12}$;
 b) halogen;
 c) CF$_3$;
 d) SR$^{12}$;
 e) phenyl or substituted phenyl wherein substituted phenyl is as defined below in the definition of R$^{12}$;
 f) COOR$^{13}$;

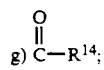

h) tetrazole;

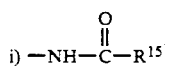

wherein R$^{15}$ is C$_1$ to C$_6$ alkyl, benzyl or phenyl;
j) —NR$^{13}$R$^{13}$;
k) —NHSO$_2$R$^{16}$ wherein R$^{16}$ is C$_1$ to C$_6$ alkyl, phenyl, or CF$_3$;

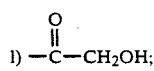

m) —SOR$^{12}$;
n) —CONR$^{13}$R$^{13}$;
o) —SO$_2$NR$^{13}$R$^{13}$;
p) —SO$_2$R$^{12}$;
q) NO$_2$;

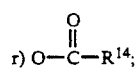

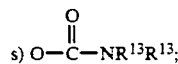

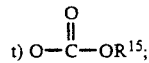

u) CN;

each R$^{12}$ is independently H; C$_1$ to C$_6$ alkyl; benzyl; phenyl or substituted phenyl wherein the substituents are C$_1$ to C$_3$ alkyl, halogen, CN, CF$_3$, COOR$^{13}$, C$_1$ to C$_4$ perfluoroalkyl; or CH$_2$COOR$^{13}$;

each R$^{13}$ is independently H, phenyl or C$_1$ to C$_6$ alkyl; and, each R$^{14}$ is independently H, (CH$_2$)$_n$COOR$^{13}$ wherein n is 0 to 4, C$_1$ to C$_6$ alkyl, CF$_3$, phenyl, or substituted phenyl wherein substituted phenyl is as defined above in the definition of R$^{12}$; or a pharmaceutically acceptable salt thereof, and a pharmaceutically acceptable carrier.

More preferred compositions of the present invention comprise compounds of the Formula I wherein:

R$^1$ is H or alkyl of 1 to 6 carbons or R$^1$ and R$^8$ taken together form a group (CH$_2$)$_v$ wherein v is 1 to 7;

R$^2$ is

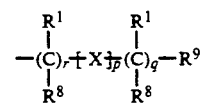

wherein:
each R$^8$ is independently H, OH, C$_1$ to C$_4$—O—alkyl or alkyl of 1 to 4 carbons; or an R$^1$ and an R$^8$ taken together form a group (CH$_2$)$_v$ wherein v is 1 to 7;

R$^9$ is COOR$^1$; CH$_2$OH; CHO; tetrazole; hydroxymethylketone;

X is O; S; SO; SO$_2$; NR$^{11}$ wherein R$^{11}$ is H, alkyl of 1 to 6 carbons, acyl of 1 to 6 carbons, CN; CR$^1$R$^8$; or the unit

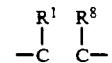

wherein the dotted line represents an optional triple bond and in which the R$^1$ and R$^8$ substituents are absent when a triple bond is present;

r and q are each independently 0 to 5 and p is 0 or 1 provided that the total of P, q and r is 2 to 4;

R$^3$ is H, alkyl of 1 to 6 carbons; phenyl or phenyl substituted by R$^4$; or C$_1$ to C$_4$ alkylphenyl or C$_1$ to C$_4$ alkylphenyl in which the phenyl is substituted by R$^4$;

R$^4$, R$^5$, R$^6$ and R$^7$ are each independently selected from:
(1) hydrogen;
(2) alkyl having 1 to 6 carbon atoms;
(3) alkenyl having 2 to 6 carbon atoms;
(4) M wherein M is
 a) OR$^{12}$;
 b) halogen;
 c) CF$_3$;
 d) SR$^{12}$;
 e) phenyl or substituted phenyl wherein substituted phenyl is as defined below in the definition of R$^{12}$;
 f) COOR$^{13}$;

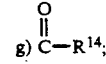

h) tetrazole;

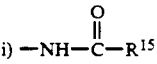

wherein R$^{15}$ is C$_1$ to C$_6$ alkyl, benzyl or phenyl;

j) —NR$^{13}$R$^{13}$;

k) —NHSO$_2$R$^{16}$ wherein R$^{16}$ is C$_1$ to C$_6$ alkyl, phenyl, or CF$_3$;

l) 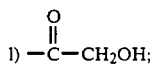

m) —SOR$^{12}$ wherein R$^{12}$ is as defined above;

n) —CONR$^{13}$R$^{13}$;

o) —SO$_2$NR$^{13}$R$^{13}$;

p) —SO$_2$R$^{12}$;

q) NO$_2$;

r) 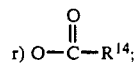

s) 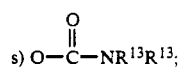

t) 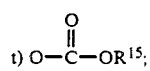

u) CN;

each R$^{12}$ is independently H; C$_1$ to C$_6$ alkyl; benzyl; phenyl or substituted phenyl wherein the substituents are C$_1$ to C$_3$ alkyl, halogen, CN, CF$_3$, COOR$^{13}$, CH$_2$COOR$^{13}$, or C$_1$ to C$_4$ perfluoroalkyl;

each R$^{13}$ is independently H, phenyl or C$_1$ to C$_6$ alkyl; and each R$^{14}$ is independently H, (CH$_2$)$_n$COOR$^{13}$ wherein n is 0 to 4, C$_1$ to C$_6$ alkyl, CF$_3$, phenyl, or substituted phenyl wherein substituted phenyl is as defined above in the definition of R$^{12}$; or a pharmaceutically acceptable salt thereof, and a pharmaceutically acceptable carrier.

Most preferred compositions of the present invention comprise compounds of the Formula I wherein:

R$^1$ is H or alkyl or 1 to 3 carbons or R$^1$ and R$^8$ taken together form a group (CH$_2$)$_v$ wherein v is 1 to 7, with the proviso that R$^1$ on the benzylic carbon attached to the indole nitrogen is H;

R$^2$ is

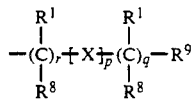

wherein:

each R$^8$ is independently H, or alkyl of 1 to 4 carbons; or an R$^1$ and an R$^8$ taken together form a group (CH$_2$)$_v$ wherein v is 1 to 7.

R$^9$ is COOR$^1$; CH$_2$OH; CHO; or tetrazole;

X is O; S; SO; SO$_2$; NR$^{11}$ wherein R$^{11}$ is H, alkyl of 1 to 6 carbons, acyl of 1 to 6 carbons, CN; CR$^1$R$^8$; or the unit

wherein the dotted line represents an optical triple bond and in which the R$^1$ and R$^8$ substituents are absent when a triple bond is present;

r and q are each independently 0 to 5 and p is 0 or 1 provided that the total of p, q and r is 2 to 3;

R$^3$ is alkyl of 1 to 6 carbons, but is not cycloalkyl;

R$^4$, R$^5$, R$^6$ and R$^7$ are each independently selected from:
(1) hydrogen;
(2) alkyl having 1 to 6 carbon atoms;
(3) M wherein M is
a) OR$^{12}$;
b) halogen;
c) CF$_3$;
d) SR$^{12}$;
e) —SOR$^{12}$;
f) —SO$_2$R$^{12}$;

g) 

wherein R$^{14}$ is H, (CH$_2$)$_n$COOR$^{13}$ wherein n is 0 to 4, C$_1$ to C$_6$ alkyl, CF$_3$, phenyl, or substituted phenyl wherein substituted phenyl is as defined above in the definition of R$^{12}$; H, C$_1$ to C$_6$ alkyl, CF$_3$, phenyl or substituted phenyl wherein substituted phenyl is as defined below in the definition of R$^{12}$;

h) CN;

each R$^{12}$ is independently H; C$_1$ to C$_6$ alkyl; benzyl; phenyl or substituted phenyl wherein the substituents are C$_1$ to C$_3$ alkyl, halogen, CN, CF$_3$, COOR$^{13}$, CH$_2$COOR$^{13}$, wherein R$^{13}$ is H, phenyl, C$_1$ to C$_6$ alkyl, or C$_1$ to C$_4$ perfluoroalkyl;

or a pharmaceutically acceptable salt thereof, and a pharmaceutically acceptable carrier.

The present invention also relates to novel compounds of Formula I represented by Formula Ia:

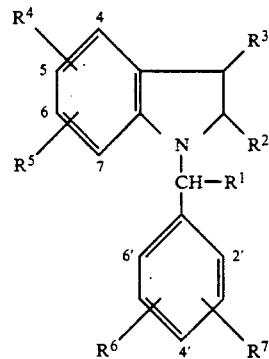

wherein:

R$^1$ is H or alkyl of 1 to 6 carbons or R$^1$ and R$^8$ taken together form a group (CH$_2$)$_v$ wherein v is 1 to 7;

R$^2$ is

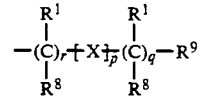

wherein:

each R$^8$ is independently H, OH, C$_1$ to C$_4$-O-alkyl, or alkyl of 1 to 4 carbons or R$^1$ and R$^8$ taken together form a group (CH$_2$)$_v$ wherein v is 1 to 7;

R$^9$ is COOR$^1$; CH$_2$OH; CHO; tetrazole; NHSO$_2$R$^{10}$ wherein R$^{10}$ is OH, alkyl or alkoxy of 1 to 6 carbons, perhaloalkyl of 1 to 6 carbons, phenyl or phenyl substituted by alkyl or alkoxy groups of 1 to 3 carbons, halogen, hydroxy, COOH, CN, formyl or acyl to 1 to 6 carbons; $CONHSO_2R^{10}$; hydroxymethylketone; CN; or $CON(R^8)_2$;

X is O; S; SO; $SO_2$; $NR^{11}$ wherein $R^{11}$ is H, alkyl of 1 to 6 carbons, acyl of 1 to 6 carbons, CN; $CR^1R^8$; or the unit $$-\underset{\underset{R^8}{|}}{\overset{\overset{R^1}{|}}{C}}\equiv\underset{\underset{}{}}{\overset{\overset{}{}}{C}}-$$

wherein the dotted line represents an optical triple bond and in which the $R^1$ and $R^8$ substituents are absent when a triple bond is present;

r and q are each independently 0 to 5 and p is 0 or 1 provided that the total of p, q and r is 2 to 6, with the proviso that when $R^1$ and $R^8$ are H, X is $CH_2$, $R^4$ is 5-methoxy and $R^6$ is halogen, then the sums of p, q and r is 3 to 6;

$R^3$ is H, alkyl of 1 to 6 carbons; phenyl or phenyl substituted by $R^4$; or $C_1$ to $C_4$ alkylphenyl or $C_1$ to $C_4$ alkylphenyl in which the phenyl is substituted by $R^4$;

$R^4$, $R^5$, $R^6$ and $R^7$ are each independently selected from:
(1) hydrogen;
(2) alkyl having 1 to 6 carbon atoms;
(3) alkenyl having 2 to 6 carbon atoms;
(4) $-(CH_2)_nM$ wherein n is 0 to 3 and M is
   a) $OR^{12}$;
   b) halogen;
   c) $CF_3$;
   d) $SR^{12}$;
   e) phenyl or substituted phenyl wherein substituted phenyl is as defined below in the definition of $R^{12}$;
   f) $COOR^{13}$;

g) $\overset{O}{\underset{\|}{C}}-R^{14}$;

h) tetrazole;

i) $-NH-\overset{O}{\underset{\|}{C}}-R^{15}$ wherein $R^{15}$ is $C_1$ to $C_6$ alkyl, benzyl or phenyl;
   j) $-NR^{13}R^{13}$;
   k) $-NHSO_2R^{16}$ wherein $R^{16}$ is $C_1$ to $C_6$ alkyl, phenyl, or $CF_3$;

l) $-\overset{O}{\underset{\|}{C}}-CH_2OH$;

m) $-SOR^{12}$;
   n) $-CONR^{13}R^{13}$;
   o) $-SO_2NR^{13}R^{13}$;
   p) $-SO_2R^{12}$;
   q) $NO_2$;

r) $O-\overset{O}{\underset{\|}{C}}-R^{14}$;

s) $O-\overset{O}{\underset{\|}{C}}-NR^{13}R^{13}$;

-continued t) $O-\overset{O}{\underset{\|}{C}}-OR^{15}$;

u) CN;

each $R^{12}$ is independently H; $C_1$ to $C_6$ alkyl; benzyl; phenyl or substituted phenyl wherein the substituents are $C_1$ to $C_3$ alkyl, halogen, CN, $CF_3$, $COOR^{13}$, $CH_2COOR^{13}$ $C_1$ to $C_3$ alkoxy, or $C_1$ to $C_4$ perfluoroalkyl;

each $R^{13}$ is independently H, phenyl or $C_1$ to $C_6$ alkyl;

each $R^{14}$ is independently H, $(CH_2)_nCOOR^{13}$ wherein n is 0 to 4, $C_1$ to $C_6$ alkyl, $CF_3$, phenyl, or substituted phenyl wherein substituted phenyl is as defined above in the definition of $R^{12}$; or a pharmaceutically acceptable salt thereof.

Preferred novel compounds of the present invention are compounds of the Formula Ia wherein:

$R^1$ is H or alkyl of 1 to 6 carbons or $R^1$ and $R^8$ taken together form a group $(CH_2)_v$ wherein v is 1 to 7;

$R^2$ is $$-\underset{\underset{R^8}{|}}{\overset{\overset{R^1}{|}}{(C)_r}}\hspace{-2pt}\big(X\big)_{\hspace{-2pt}p}\hspace{-2pt}\underset{\underset{R^8}{|}}{\overset{\overset{R^1}{|}}{(C)_q}}-R^9$$

wherein:
each $R^8$ is independently H, OH, $C_1$ to $C_4$-O-alkyl, or alkyl of 1 to 4 carbons or $R^1$ and $R^8$ taken together form a group $(CH_2)_v$ wherein v is 1 to 7;

$R^9$ is $COOR^1$; $CH_2OH$; CHO; tetrazole; $CONHSO_2R^{10}$ wherein $R^{10}$ is OH, alkyl or alkoxy of 1 to 6 carbons, perhaloalkyl of 1 to 6 carbons, phenyl or phenyl substituted by alkyl or alkoxy groups of 1 to 3 carbons, halogen, hydroxy, COOH, CN, formyl or acyl to 1 to 6 carbons; hydroxymethylketone; CN; or $CON(R^8)_2$;

X is O; S; SO; $SO_2$; $NR^{11}$ wherein $R^{11}$ is H, alkyl of 1 to 6 carbons, acyl of 1 to 6 carbons, CN; $CR^1R^8$; or the unit $$-\underset{\underset{}{}}{\overset{\overset{R^1}{|}}{C}}\equiv\underset{\underset{}{}}{\overset{\overset{R^8}{|}}{C}}-$$

wherein the dotted line represents an optional triple bond and in which the $R^1$ and $R^8$ substituents are absent when a triple bond is present;

r and q are each independently 0 to 5 and p is 0 or 1 provided that the total of p, q and r is 2 to 4, with the proviso that when $R^1$ and $R^8$ are H, X is $CH_2$, $R^4$ is 5-methoxy and $R^6$ is halogen, then the sums of p, q and r is 3 to 4;

$R^3$ is H, alkyl of 1 to 6 carbons; phenyl or phenyl substituted by $R^4$; or $C_1$ to $C_4$ alkylphenyl or $C_1$ to $C_4$ alkylphenyl in which the phenyl is substituted by $R^4$;

$R^4$, $R^5$, $R^6$ and $R^7$ are each independently selected from:
(1) hydrogen;
(2) alkyl having 1 to 6 carbon atoms;
(3) alkenyl having 2 to 6 carbon atoms;
(4) $-(CH_2)_nM$ wherein n is 0 or 1 and M is
   a) $OR^{12}$;
   b) halogen;
   c) $CF_3$;
   d) $SR^{12}$;

e) phenyl or substituted phenyl wherein substituted phenyl is as defined below in the definition of $R^{12}$;

f) $COOR^{13}$;

g) 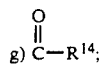

wherein $R^{14}$ is H, $(CH_2)_nCOOR^{13}$ wherein n is 0 to 4, $C_1$ to $C_6$ alkyl, $CF_3$, phenyl, or substituted phenyl wherein substituted phenyl is as defined below in the definition of $R^{12}$;

h) tetrazole;

i) 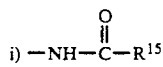

wherein $R^{15}$ is $C_1$ to $C_6$ alkyl, benzyl or phenyl;

j) $-NR^{13}R^{13}$;

k) $-NHSO_2R^{16}$ wherein $R^{16}$ is $C_1$ to $C_6$ alkyl, phenyl, or $CF_3$;

l) 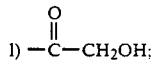

m) $-SOR^{12}$;
n) $-CONR^{13}R^{13}$;
o) $-SO_2NR^{13}R^{13}$;
p) $-SO_2R^{12}$;
q) $NO_2$;

r) 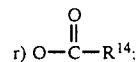

s) 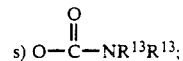

t) 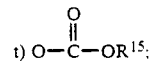

u) CN;

each $R^{12}$ is independently H; $C_1$ to $C_6$ alkyl; benzyl; phenyl or substituted phenyl wherein the substituents are $C_1$ to $C_3$ alkyl, halogen, CN, $CF_3$, $COOR^{13}$, $CH_2COOR^{13}$ $C_1$ to $C_3$ alkoxy $C_1$ to $C_4$ perfluoroalkyl;

each $R^{13}$ is independently H, phenyl or $C_1$ to $C_6$ alkyl;

each $R^{14}$ is independently H, $(CH_2)_nCOOR^{13}$ wherein n is 0 to 4, $C_1$ to $C_6$ alkyl, $CF_3$, phenyl, or substituted phenyl wherein substituted phenyl is as defined above in the definition of $R^{12}$; or a pharmaceutically acceptable salt thereof.

More preferred novel compounds of the present invention are compounds of the formula Ia wherein:

$R^1$ is H or alkyl of 1 to 6 carbons or $R^1$ and $R^8$ taken together form a group $(CH_2)_v$ wherein v is 1 to 7;

$R^2$ is

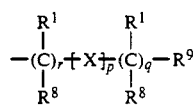

wherein:

each $R^8$ is independently H, OH, $C_1$ to $C_4$-O-alkyl, or alkyl of 1 to 4 carbons or $R^1$ and $R^8$ taken together form a group $(CH_2)_v$ wherein v is 1 to 7;

$R^9$ is $COOR^1$; $CH_2OH$; CHO; tetrazole; hydroxymethylketone;

X is O; S; SO; $SO_2$; $NR^{11}$ wherein $R^{11}$ is H, alkyl of 1 to 6 carbons, acyl of 1 to 6 carbons, CN; $CR^1R^8$; or the unit

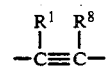

wherein the dotted line represents an optional triple bond and in which the $R^1$ and $R^8$ substituents are absent when a triple bond is present;

r and q are each independently 0 to 5 and p is 0 or 1 provided that the total of p, q and r is 2 to 4, with the proviso that when $R^1$ and $R^8$ are H, X is $CH_2$, $R^4$ is 5-methoxy and $R^6$ is halogen, then the sums of p, q and r is 3 to 4;

$R^3$ is H, alkyl of 1 to 6 carbons; phenyl or phenyl substituted by $R^4$; or $C_1$ to $C_4$ alkylphenyl or $C_1$ to $C_4$ alkylphenyl in which the phenyl is substituted by $R^4$;

$R^4$, $R^5$, $R^6$ and $R^7$ are each independently selected from:

(1) hydrogen;
(2) alkyl having 1 to 6 carbon atoms;
(3) alkenyl having 2 to 6 carbon atoms;
(4) M wherein M is
a) $OR^{12}$;
b) halogen;
c) $CF_3$;
d) $SR^{12}$;
e) phenyl or substituted phenyl wherein substituted phenyl is as defined below in the definition of $R^{12}$;
f) $COOR^{13}$;

g) 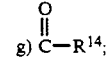

h) tetrazole;

i) 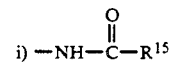

wherein $R^{15}$ is $C_1$ to $C_6$ alkyl, benzyl or phenyl;

j) $-NR^{13}R^{13}$;

k) $-NHSO_2R^{16}$ wherein $R^{16}$ is $C_1$ to $C_6$ alkyl, phenyl, or $CF_3$;

l) 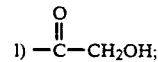

m) $-SOR^{12}$;
n) $-CONR^{13}R^{13}$;
o) $-SO_2NR^{13}R^{13}$;
p) $-SO_2R^{12}$;
q) $NO_2$;

r) 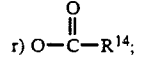

s) 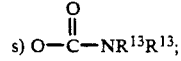

-continued

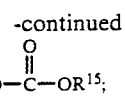

u) CN;

each $R^{12}$ is independently H; $C_1$ to $C_6$ alkyl; benzyl; phenyl or substituted phenyl wherein the substituents are $C_1$ to $C_3$ alkyl, halogen, CN, $CF_3$, $COOR^{13}$, $CH_2COOR^{13}$, $C_1$ to $C_3$ alkoxy or $C_1$ to $C_4$ perfluoroalkyl;

each $R^{13}$ is independently H, phenyl or $C_1$ to $C_6$ alkyl; and each $R^{14}$ is H, $(CH_2)_nCOOR^{13}$ wherein n is 0 to 4, $C_1$ to $C_6$ alkyl, $CF_3$, phenyl, or substituted phenyl wherein substituted phenyl is as defined above in the definition of $R^{12}$; or a pharmaceutically acceptable salt thereof.

Most preferred novel compounds of the present invention are compounds of the formula Ia wherein:

$R^1$ is H or alkyl of 1 to 3 carbons or $R^1$ and $R^8$ taken together form a group $(CH_2)_v$ wherein v is 1 to 7, with the proviso that $R^1$ on the benzylic carbon attached to the indole nitrogen is H;

$R^2$ is

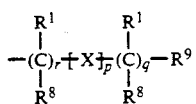

wherein:

each $R^8$ is independently H, OH, $C_1$ to $C_4$-O-alkyl or alkyl of 1 to 4 carbons or $R^1$ and $R^8$ taken together form a group $(CH_2)_v$ wherein v is 1 to 7;

$R^9$ is $COOR^1$; $CH_2OH$; CHO; or tetrazole;

X is O; S; SO; $SO_2$; $NR^{11}$ wherein $R^{11}$ is H, alkyl of 1 to 6 carbons, acyl of 1 to 6 carbons, CN; $CR^1R^8$; or the unit

wherein the dotted line represents an optional triple bond and in which the $R^1$ and $R^8$ substituents are absent when a triple bond is present;

r and q are each independently 0 to 5 and p is 0 or 1 provided that the total of p, q and r is 2 to 3, with the proviso that when $R^1$ and $R^8$ are H, X is $CH_2$, $R^4$ is 5-methoxy and $R^6$ is halogen, then the sum of r, p and q is 3 to 4;

$R^3$ is alkyl of 1 to 6 carbons, but not cycloalkyl;

$R^4$, $R^5$, $R^6$ and $R^7$ are each independently selected from:

(1) hydrogen;
(2) alkyl having 1 to 6 carbon atoms;
(3) M wherein M is
a) $OR^{12}$;
b) halogen;
c) $CF_3$;
d) $SR^{12}$;
e) $-SOR^{12}$;
f) $-SO_2R^{12}$;

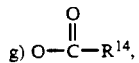

wherein $R^{14}$ is H, $C_1$ to $C_6$ alkyl, $CF_3$, phenyl or substituted phenyl wherein substituted phenyl is as defined below in the definition of $R^{12}$;

h) CN;

each $R^{12}$ is independently H; $C_1$ to $C_6$ alkyl; benzyl; phenyl or substituted phenyl wherein the substituents are $C_1$ to $C_3$ alkyl, halogen, CN, $CF_3$, $COOR^{13}$, $CH_2COOR^{13}$, $C_1$ to $C_3$ alkoxy; or $C_1$ to $C_4$ perfluoroalkyl;

each $R^{13}$ is independently H, phenyl or $C_1$ to $C_6$ alkyl; or a pharmaceutically acceptable salt thereof.

Most-particularly preferred novel compounds of the present invention are compounds of the formula Ia wherein:

$R^1$ is H or alkyl of 1 to 3 carbons, with the proviso that $R^1$ on the benzylic carbon attached to the indole nitrogen is H;

$R^2$ is

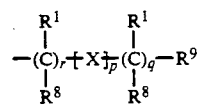

wherein:

each $R^8$ is independently H or alkyl of 1 to 4 carbons, with the proviso that at least one of the $R^1$ or $R^8$ substituents in $R^2$ is not hydrogen;

$R^9$ is COOH; $CH_2OH$; CHO; or tetrazole;

X is $CR^1R^8$;

r and q are each independently 0 to 3 and p is 0 or 1 provided that the total of p, q and r is 2 to 3;

$R^3$ is alkyl of 1 to 6 carbons, but not cycloalkyl;

$R^4$, $R^5$, $R^6$ and $R^7$ are each independently selected from:

(1) hydrogen;
(2) alkyl having 1 to 6 carbon atoms;
(3) M wherein M is
a) $OR^{12}$;
b) halogen;
c) $CF_3$;
d) $SR^{12}$;
e) $-SOR^{12}$;
f) $-SO_2R^{12}$;

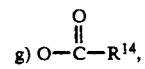

wherein $R^{14}$ is H, $C_1$ to $C_6$ alkyl, $CF_3$, phenyl or substituted phenyl wherein substituted phenyl is as defined below in the definition of $R^{12}$;

h) CN;

each $R^{12}$ is independently H; $C_1$ to $C_6$ alkyl; or benzyl; or a pharmaceutically acceptable salt thereof.

Other most-particularly preferred novel compounds of the present invention are compounds of the formula Ia wherein:

$R^1$ is H or alkyl of 1 to 3 carbons, with the proviso that $R^1$ on the benzylic carbon attached to the indole nitrogen is H;

$R^2$ is

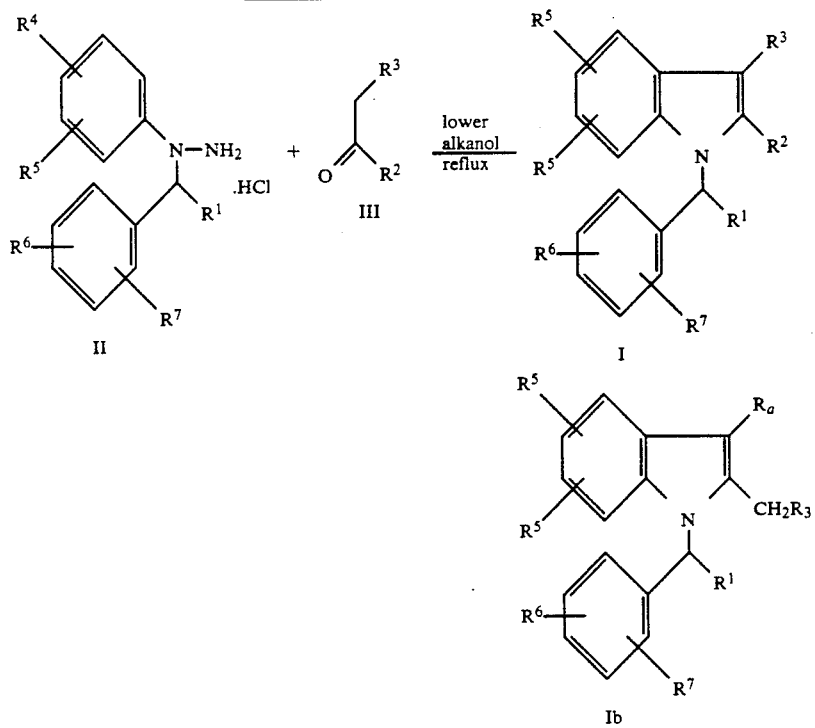

Scheme I
Preparation of Formula I Compounds

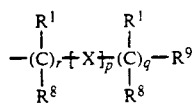

wherein:
each $R^8$ is independently H or alkyl of 1 to 4 carbons;
$R^9$ is COOH; CH$_2$OH; CHO; or tetrazole;
X is O; S; SO; or SO$_2$;
r and q are each independently 0 to 3 and p is 1 provided that the total of p, q and r is 2 to 3;
$R^3$ is alkyl of 1 to 6 carbons, but not cycloalkyl;
$R^4$, $R^5$, $R^6$ and $R^7$ are each independently selected from:
(1) hydrogen;
(2) alkyl having 1 to 6 carbon atoms;
(3) M wherein M is
a) OR$^{12}$;
b) halogen;
c) CF$_3$;
d) SR$^{12}$;
e) —SOR$^{12}$;
f) —SO$_2$R$^{12}$;

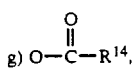

wherein $R^{14}$ is H, C$_1$ to C$_6$ alkyl, CF$_3$, phenyl or substituted phenyl wherein substituted phenyl is as defined below in the definition of $R^{12}$;
h) CN;
each $R^{12}$ is independently H; C$_1$ to C$_6$ alkyl; or benzyl; or a pharmaceutically acceptable salt thereof.

The following reaction schemes illustrate the preparation of the compounds of the present invention:

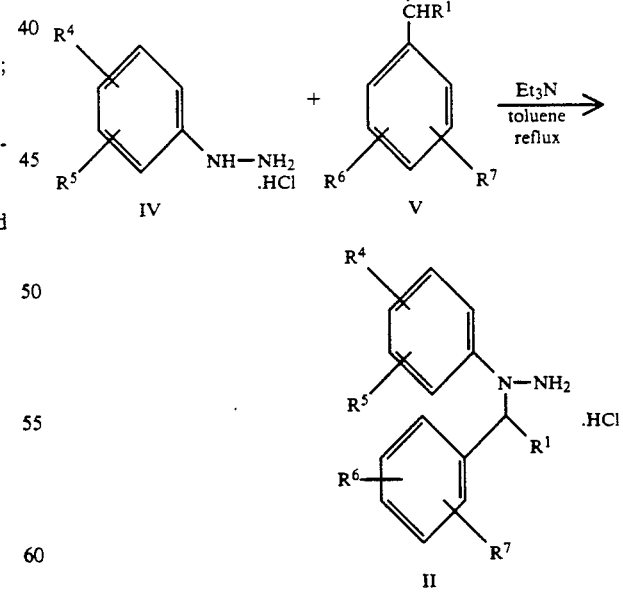

Scheme III
Preparation of Hydrazine Derivatives (II)

With regard to Scheme I, the alkanol solvent can have an important effect on the course of the reaction. With some of the ketones III, the final product may contain a mixture of the isomers I and Ib. Formation of the undesired Ib is minimized by using ispropanol or tert-butanol in place of methanol or ethanol.

The sequence described above is an application of the Fischer Indole Synthesis. Numerous indole syntheses are described in reviews, such as, for example "Heterocyclic Compounds" Volume 25, Parts I, II, III, W. J. Houlihan (Ed.), Interscience, J. Wiley & Sons, N.Y., 1979. Appropriate manipulations of functional groups using sequences described in such reviews will lead to the compounds of the present invention. Another useful sequence is shown in Scheme III.

The Bischler Indole Synthesis used in the sequence described for the synthesis of compounds of the present invention envisages the alkylation of an appropriately substituted halo or tosyloxy ketone (VII) by an appropriately substituted aniline derivative (VI), in an alcoholic solvent. The condensation step is effected through the use of a Lewis Acid or mineral acid. The indole derivative so produced (IX) may then be alkylated by an aralkylhalide to product I.

The following ketones (1-7) of structure III are known in the art:

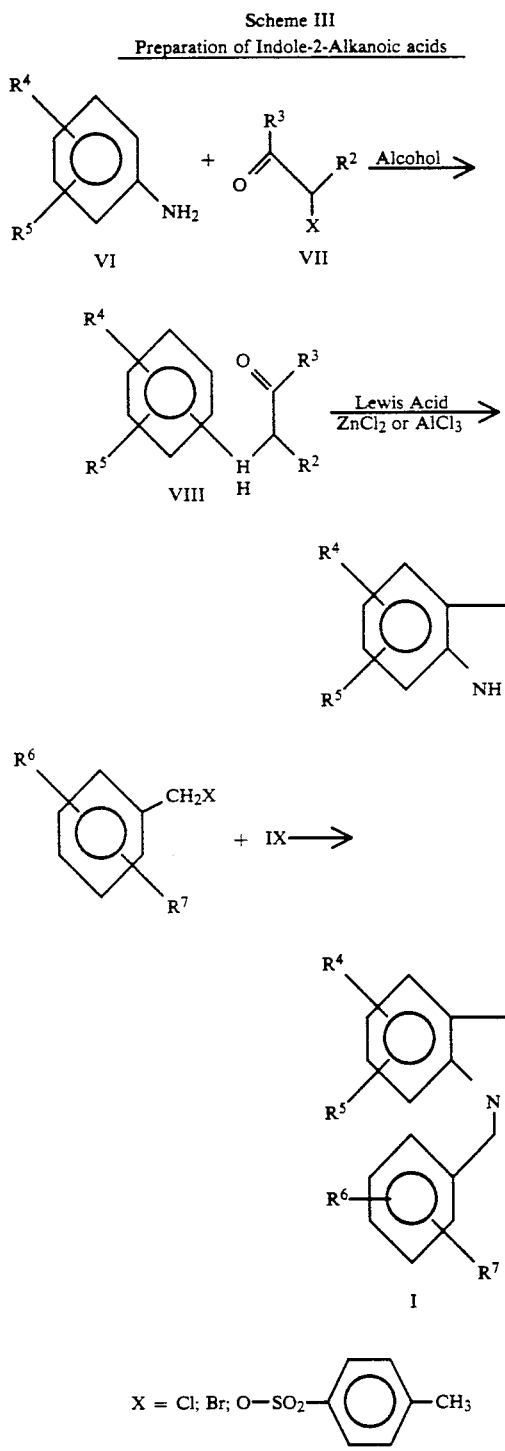

TABLE 1

Ketones of Formula III

| No. | Structure | Reference |
|---|---|---|
| 1. | 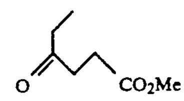 | Methyl 4-oxohexanoate: B. L. Feringa and W. Dannenberg, Synth. Commun., 13, 509-514 (1983). |
| 2. | 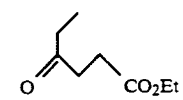 | Ethyl 4-oxohexanoate: D. A. Wehrli and V. Chu, Org. Synth., 58, 79-82 (1978). |
| 3. | 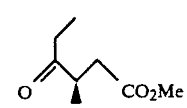 | 3-Methyl-4-oxohexanoate: A. P. Cowling and J. Mann, J. Chem. Soc., Chem. Commun., 1006-1007 (1978). |
| 4. | 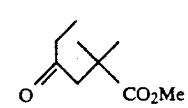 | Methyl 2,2-dimethyl-4-oxohexanoate: R. Scarpati, G. Scherillo, F. Imperato and R. A. Nicolaus, Gazz. Chim. Ital., 97, 654-664 (1967). |
| 5. | 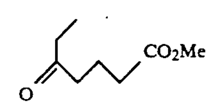 | Methyl 5-oxoheptanoate: M. K. Eberle and G. G. Kahle, Tetrahedron Lett., 21, 2303-2304 (1980). |
| 6. | 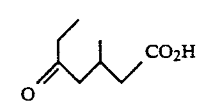 | 3-Methyl-5-oxoheptanoic acid: C. Conti, A. Niccoli and R. Rossi, Chim. Ind. (Milan) 58; 877 (1976). |
| 7. | 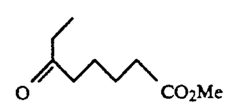 | Methyl 6-oxooctanoate: T. Terasawa and T. Okada, Tetrahedron 33, 595-598 (1977). |
| 8. | 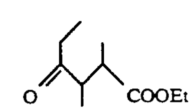 | Ethyl 2,3-dimethyl-4-oxohexanoate |

Examples of Formula I compounds useful in the pharmaceutical compositions of the present invention are tabulated below. The numbers preceding the $R^4$, $R^5$ $R^6$, and $R^7$ definitions indicate the substituent position in the structure. Standard abbreviations such as Me for methyl, Et for ethyl, Pr for propyl, Bu for butyl, Ac for acetyl, and Ph for phenyl are used. Compounds 3 to 72 are novel compounds.

TABLE 2

Compounds of the Formula I

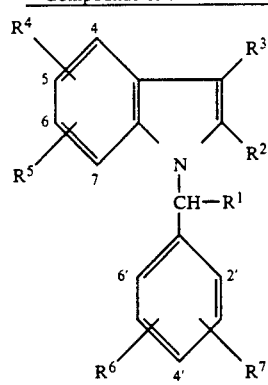

| Compound No. | $R^1$ | $R^2$ | $R^3$ | $R^4$ | $R^5$ | $R^6$ | $R^7$ |
|---|---|---|---|---|---|---|---|
| 1 | H | $(CH_2)_2CO_2H$ | Me | 5-OMe | H | 4'-Cl | H |
| 2 | H | $(CH_2)_2CO_2Me$ | Me | 5-OMe | H | 4'-Cl | H |
| 3 | H | $(CH_2)_2CO_2H$ | Me | 5-F | H | 4'-Cl | H |
| 4 | H | $(CH_2)_2CO_2H$ | Me | 4-Cl | 6-Cl | 4'-Cl | H |
| 5 | H | $(CH_2)_2CO_2H$ | Me | 4-OMe | H | 4'-Cl | H |
| 6 | H | $(CH_2)_2CO_2H$ | Me | 6-OMe | H | 4'-Cl | H |
| 7 | H | $(CH_2)_2CO_2H$ | Me | 4-Me | H | 4'-Cl | H |
| 8 | H | $(CH_2)_2CO_2H$ | Me | 6-Me | H | 4'-Cl | H |
| 9 | H | $(CH_2)_4CO_2H$ | Me | 5-OMe | H | 4'-Cl | H |
| 10 | H | $(CH_2)_2CO_2H$ | Me | 5-Me | H | 4'-Cl | H |
| 11 | H | $(CH_2)_3CO_2H$ | Me | 5-OMe | H | 4'-Cl | H |
| 12 | H | $(CH_2)_2CO_2H$ | Me | 5-OH | H | 4'-Cl | H |
| 13 | H | $(CH_2)_2CO_2H$ | Me | 5-Cl | H | 4'-Cl | H |
| 14 | H | $(CH_2)_2CO_2H$ | Me | H | H | 4'-Cl | H |
| 15 | H | $(CH_2)_2CO_2H$ | Me | 5-Br | H | 4'-Cl | H |
| 16 | H | $(CH_2)_2CO_2H$ | Me | 5-OMe | H | 4'-S(=O)-Me | H |
| 17 | H | $(CH_2)_2CO_2H$ | Me | 5-OMe | H | 4'-SMe | H |
| 18 | H | $(CH_2)_3CO_2H$ | Me | 5-OMe | H | 4'-SMe | H |
| 19 | H | $(CH_2)_3CO_2H$ | Me | 5-F | H | 4'-Cl | H |
| 20 | H | $(CH_2)_2CO_2H$ | Me | 5-F | H | 4'-SMe | H |
| 21 | H | $(CH_2)_2CO_2H$ | Me | 5-F | H | 4'-S(=O)-Me | H |
| 22 | H | $CH(Me)CH_2CO_2H$ | Me | 5-OMe | H | 4'-Cl | H |
| 23 | H | $CH_2OCH_2CO_2H$ | Me | 5-OMe | H | 4'-Cl | H |
| 24 | H | $(CH_2)_2CO_2H$ | Me | 5-OAc | H | 4'-Cl | H |
| 25 | H | $CH_2CH(Me)CH_2CO_2H$ | Me | 5-OMe | H | 4'-Cl | H |
| 26 | H | $(CH_2)CH(Me)CH_2CO_2H$ | H | 5-F | H | 4'-Cl | H |
| 27 | H | $CH_2C(Me)_2CO_2H$ | H | 5-OMe | H | 4'-Cl | H |
| 28 | H | $(CH_2)_3CO_2H$ | Me | 5-F | H | 4'-SMe | H |
| 29 | H | $(CH_2)_2CO_2H$ | Me | 5-OMe | H | H | H |
| 30 | H | $(CH_2)_2CO_2H$ | Me | H | H | H | H |
| 31 | H | $(CH_2)_2CO_2H$ | Me | 5-OMe | H | 4'-$CF_3$ | H |
| 32 | H | $(CH_2)_2CO_2H$ | Me | 5-OMe | H | 4-SMe | H |
| 33 | H | $(CH_2)_2CO_2H$ | Me | 5-OMe | H | 4-SMe→O | H |
| 34 | H | $(CH_2)_2CO_2H$ | Me | 5-OMe | H | 4'-$SMe(=O)(=O)$ | H |
| 35 | H | $(CH_2)_2CO_2H$ | Me | 5-F | H | 4'-Cl | H |
| 36 | H | $(CH_2)_2CO_2H$ | Me | 5-Cl | H | 4'-Cl | H |
| 37 | H | $(CH_2)_2CO_2H$ | Me | 5-Br | H | 4'-Cl | H |
| 38 | Me | $(CH_2)_2CO_2H$ | Me | 5-OMe | H | 4'-Cl | H |
| 39 | H | $(CH_2)_2CO_2H$ | Et | 5-OMe | H | 4'-Cl | H |
| 40 | H | $(CH_2)_2CO_2H$ | Me | 5-OH | H | 4'-Cl | H |
| 41 | H | $(CH_2)_2CO_2H$ | Me | 5-OAc | H | 4'-Cl | H |
| 42 | H | $(CH_2)_2CO_2H$ | Me | 4-OMe | H | 4'-Cl | H |
| 43 | H | $(CH_2)_2CO_2H$ | Me | 4-Cl | H | 4'-Cl | H |
| 44 | H | $(CH_2)_2CO_2H$ | Me | 4-Cl | 6-Cl | 4'-$CF_3$ | H |

TABLE 2-continued

Compounds of the Formula I

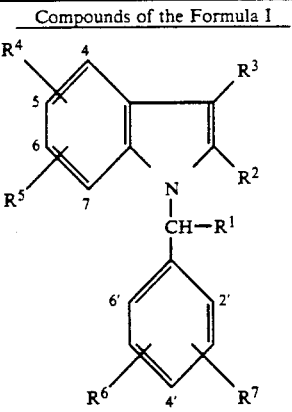

| Compound No. | R¹ | R² | R³ | R⁴ | R⁵ | R⁶ | R⁷ |
|---|---|---|---|---|---|---|---|
| 45 | H | (CH₂)₃CO₂H | Me | 5-OMe | 4-Cl | H | H |
| 46 | same as 2 to 16 with R² being (CH₂)₃COOH | | | | | | |
| 47 | H | CH(Me)CH₂CO₂H | Me | 5-OMe | 4-Cl | H | H |
| 48 | same as 2 to 16 with R² being CH(Me)CH₂COOH | | | | | | |
| 49 | H | CH₂—CH(Me)—COOH | Me | 5-OMe | H | 4'-Cl | H |
| 50 | same as 2 to 16 with R² being CH₂—CH(Me)COOH | | | | | | |
| 51 | H | CH(Me)(CH₂)₂—COOH | Me | 5-OMe | H | 4'-Cl | H |
| 52 | same as 2 to 16 with R² being CH(Me)(CH₂)₂—COOH | | | | | | |
| 53 | H | CH₂—CH(Me)CH₂COOH | Me | 5-OMe | H | 4'-CL | H |
| 54 | same as 2 to 16 with R² being CH₂—CH(Me)—CH₂—COOH | | | | | | |
| 55 | H | CH₂CH₂CH(Me)—COOH | Me | 5-OMe | H | 4'-Cl | H |
| 56 | same as 2 to 16 with R² being (CH₂)₂—CH(Me)COOH | | | | | | |
| 57 | H | CH₂—C(Me)₂—COOH | Me | 5-OMe | H | 4'-Cl | H |
| 58 | same as 2 to 16 with R² being CH₂—C(Me)₂—COOH | | | | | | |
| 59 | H | CH₂—C(Me)₂CH₂COOH | Me | 5-OMe | H | 4'Cl | H |
| 60 | same as 2 to 16 with R² being CH₂—C(Me)₂—CH₂—COOH | | | | | | |
| 61 | H | (CH₂)₂—C(Me)₂—COOH | Me | 5-OMe | H | 4'Cl | H |
| 62 | same as 2 to 16 with R² being (CH₂)₂—C(Me)₂—COOH | | | | | | |
| 63 | H | CH₂—OCH₂COOH | Me | 5-OMe | H | 4'Cl | H |
| 64 | same as 2 to 16 with R² being CH₂—OCH₂COOH | | | | | | |
| 65 | H | CH₂—S—CH₂CO₂H | Me | 5-OMe | H | 4'Cl | H |
| 66 | H | CH₂—S(=O)—CH₂CO₂H | Me | 5-OMe | H | 4'Cl | H |
| 67 | H | CH₂S(=O)₂—CH₂CO₂H | Me | 5-OMe | H | 4'Cl | H |
| 68 | same as 2 to 16 with R² being CH₂—S—CH₂CO₂H | | | | | | |
| 69 | same as 2 to 16 with R² being CH₂—S(=O)—CH₂CO₂H | | | | | | |
| 70 | H | C(CH₃)₂CH₂CO₂H | Me | 5-OMe | H | 4'Cl | H |
| 71 | H | CH₂N(CN)—CHCH₂CO₂H | Me | 5-OMe | H | 4'Cl | H |
| 72 | same as 2 to 16 with R² being CH₂—N(CN)—CH₂CO₂H | | | | | | |
| 73 | same as 2 to 16 with R² being CH(CH₃)₂COOH | | | | | | |
| 74 | same as 2 to 16 with R² being CH(CH₃)C(CH₃)₂CH₂COOH | | | | | | |

Specific Examples of the Formula I compounds are the following, all but the first being novel:

3-[1-(4-chlorobenzyl)-3-methyl-5-methoxyindol-2-yl]propionic acid;
3-[1-(4-chlorobenzyl)-3-methyl-5-fluoroindol-2-yl]propionic acid;
3-[1-(4-chlorobenzyl)-3,4-dimethylindol-2-yl]propionic acid;
4-[1-(4-chlorobenzyl)-3-methyl-5-methoxyindol-2-yl]butanoic acid;
3-[1-(4-chlorobenzyl)-3-methyl-5-hydroxyindol-2-yl]propionic acid;
3-[1-(4-chlorobenzyl)-3-methylindol-2-yl]propionic acid;
3-[1-(4-methylthiobenzyl)-3-methyl-5-methoxyindol-2-yl]propionic acid;
3-[1-(4-methylthiobenzyl)-3-methyl-5-fluoroindol-2-yl]propionic acid;
3-[1-(4-methylsulfinylbenzyl)-3-methyl-5-methoxyindol-2-yl]propionic acid;
4-[1-(4-methylthiobenzyl)-3-methyl-5-methoxyindol-2yl]butanoic acid;
4-[1-(4-chlorobenzyl)-3-methyl-5-fluoroindol-2-yl]butanoic acid;
1-[1-(4-chlorobenzyl)-3-methyl-5-methoxyindol-2-yl]methoxy acetic acid;
3-[1-(4-chlorobenzyl)-3-methyl-5-methoxyindol-2-yl]-2,2-dimethylpropanoic acid;
3-[1-(4-chlorobenzyl)-3-methyl-5-methoxyindol-2-yl]-3-methylpropanoic acid;
3-methyl-4-[1-(4-chlorobenzyl)-5-methoxy-3-methylindol-2-yl]butanoic acid;
3-methyl-4-[1-(4-chlorobenzyl)-5-fluoro-3-methylindol-2-yl]butanoic acid;
3-[1-(4-chlorobenzyl)-3-methyl-5-fluoro-2-indolyl]-2,2-dimethyl propanoic acid.

Further examples include:

4-[1-(4-chlorobenzyl-5-fluoro-3-methyl-1H-indol-2-yl]-2,4,3,3-tetramethyl butanoic acid;
4-[1-(4-chlorobenzyl-5-fluoro-3-methyl-1H-indol-2-yl]-4,3,3-trimethyl butanoic acid;
4-[1-(4-chlorobenzyl-5-fluoro-3-methyl-1H-indol-2-yl]-2,2,3-trimethyl butanoic acid;
4-[1-(4-chlorobenzyl-5-fluoro-3-methyl-1H-indol-2-yl]-2,3,3-trimethyl butanoic acid;
4-[1-(4-chlorobenzyl-5-methoxy-3-methyl-1H-indol-2-yl]-2,2,3-trimethyl butanoic acid;
4-[1-(4-chlorobenzyl-5-ethoxy-3-methyl-1H-indol-2-yl]-2,2,3-trimethyl butanoic acid;
4-[1-(4-chlorobenzyl-5-chloro-3-methyl-1H-indol-2-yl]-2,2,3-trimethyl butanoic acid;
4-[1-(4-chlorobenzyl-3-methyl-5-trifluoromethyl-1H-indol-2-yl]-2,4,3,3-tetramethyl butanoic acid;
4-[1-(4-chlorobenzyl-3-methyl-5-trifluoromethylthio-1H-indol-2-yl]-2,4,3,3-tetramethyl butanoic acid;
3-[1-(4-chlorobenzyl)-5-ethoxy-3-methyl-1H-indol-2-yl]-2,2,3-trimethyl propanoic acid;
3-[1-(4-chlorobenzyl)-5-ethoxy-3-methyl-1H-indol-2-yl]-2,3,3-trimethyl propanoic acid;
3-[1-(4-chlorobenzyl)-5-ethoxy-3-methyl-1H-indol-2-yl]-2,2,3,3-tetramethyl propanoic acid;
3-[1-(4-chlorobenzyl)-5-methoxy-3-methyl-1H-indol-2-yl]-2,2,3-trimethyl propanoic acid;
3-[1-(4-chlorobenzyl)-5-fluoro-3-methyl-1H-indol-2-yl]-2,2,3-trimethyl propanoic acid;
3-[1-(4-chlorobenzyl)-5-chloro-3-methyl-1H-indol-2-yl]-2,2,3-trimethyl propanoic acid;
3-(1-p-chlorobenzyl-3-methyl-5-methoxyindol-2-yl)-2,2-diethyl propanoic acid;
3-[1-(4-chlorobenzyl)-3-methyl-5-fluoroindol-2-yl]-2,2-diethyl propanoic acid;
3-[1-(4-chlorobenzyl)-3-methyl-5-fluoroindol-2-yl]-2-ethyl propanoic acid;
3-[1-(4-chlorobenzyl)-3-ethyl-5-fluoroindol-2-yl]-3-methyl propanoic acid; and
3-[1-(4-chlorobenzyl-3-methyl-5-methoxy-2-indolyl]-pentanoic acid.

In those instances when asymmetric centers are present, more than one stereoisomer is possible, and all possible isomeric forms are deemed to be included within the planar structural representations shown. Optically active (R) and (S) isomers may be resolved using conventional techniques known to the skilled artisan.

The prostaglandin antagonist properties of the compounds of the present invention can be demonstrated by a number of biological assays, one of which, inhibition of platelet aggregation, is described below.

Inhibition of Induced Threshold Aggregation of Human Platelets

Human platelet rich plasma (PRP) is prepared from venous blood of male volunteers who have taken no medication for ten days prior to test. Blood is transferred into plastic centrifuge tubes containing 3.8% Trisodium Citrate in 0.9% NaCl (in a ratio of blood to anticoagulant of 9:1), mixed by gentle inversion, and centrifuged at room temperature for ten minutes at 116 g. The supernatant (PRP) is transferred into plastic tubes. Platelet poor plasma (PPP) is obtained by centrifuging the residual blood cells at 4000 g for ten minutes. PRP is left to stand at least one half hour prior to testing.

Platelet Aggregation is measured using a Payton Aggregometer and Recorder. Following calibration of the instrument, a cuvette containing PRP (225 microliters) is incubated for three minutes at 37° C. Drug vehicle (control), or a drug concentration is then added in a volume of 0.5 microliter. After one minute, the aggregating agent (U44069, 9,11-dideoxy-9α,11α-epoxymethano $PGF_{2@}$) is added to the cuvette in a volume of 25 microliters. Recording is continued until the maximal response is obtained.

The threshold (approximately 20–30% of maximum) aggregation concentration of the agonist to be used is first determined in the presence of the drug vehicle (control). Test compounds are then assayed at 10 or 30 micrograms/ml initially, and if active, are further tested in order to determine the concentration range at which 20–80% of the threshold aggregatory response is inhibited. All drugs are dissolved in dimethylsulfoxide.

The height of the aggregation response (measured in divisions of the recorder paper, 1 division=2.5 mm) in the presence of the drug is recorded, and calculated as percent inhibition of the mean height of the control threshold responses. The $IC_{50}$ (drug concentration which inhibits 50% of the aggregatory response) is obtained by regression analysis.

Compounds of Formula I or Ia can be tested using the following assay to determine their mammalian leukotriene biosynthesis inhibiting activity.

Rat Peritoneal Polymorphonuclear (PMN)
Leukocyte Assay

Rats under ether anesthesia are injected (i.p.) with 8 ml of a suspension of sodium caseinate (6 grams in ca. 50 ml water). After 15-24 hr. the rats are sacrificed ($CO_2$) and the cells from the peritoneal cavity are recovered by lavage with 20 ml of buffer (Eagles MEM containing 30 mM HEPES adjusted to pH 7.4 with NaOH). The cells are pelleted ($350 \times g$, 5 min.), resuspended in buffer with vigorous shaking, filtered, through lens paper, recentrifuged and finally suspended in buffer at a concentration of 10 cells/ml. A 500 $\mu$l aliquot of PMN suspension and test compound are preincubated for 2 minutes at 37° C., followed by the addition of 10 $\mu$M A-23187. The suspension is stirred for an additional 4 minutes then bioassayed for $LTB_4$ content by adding an aliquot to a second 500 $\mu$l portion of the PMN at 37° C. The $LTB_4$ produced in the first incubation causes aggregation of the second PMN, which is measured as a change in light transmission. The size of the assay aliquot is chosen to give a submaximal transmission change (usually $-70\%$) for the untreated control. The percentage inhibition of $LTB_4$ formation is calculated from the ratio of transmission change in the sample to the transmission change in the compound-free control.

The cytoprotective activity of a compound may be observed in both animals and many by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay.

A. Ethanol-Induced Gastric Ulcer Assay

Twenty-four hour fasted Sprague-Dawley (S.D.) rats are perorally (p.o.) dosed with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosae are examined for resulting lesions.

B. Indomethacin-Induced Ulcer Assay

Indomethacin, 10 mg/kg p.o., is used to induce ulcers in 24 hour fasted S.D. rats. Fifteen minutes prior to indomethacin administration, groups of rats each receive either an aqueous vehicle (5% by weight methylcellulose) or the test compound at various doses perorally. Four hours later the animals are sacrificed and stomach mucosae are examined for resulting ulcers.

The magnitude of a prophylactic or therapeutic dose of a compound of Formula I or Ia will, of course, vary with the nature of the severity of the condition to be treated and with the particular compound of Formula I or Ia and its route of administration. In general, the daily dose range for anti-asthmatic, anti-allergic, anti-inflammatory, or anti-thrombotic use lies within the range of from about 0.01 mg to about 100 mg per kg body weight of a mammal.

The exact amount of a compound of Formula I or Ia to be used as a cytoprotective agent will depend on, inter alia, whether it is being administered to heal damaged cells or to avoid future damage, on the nature of the damaged cells (e.g., gastro-intestinal ulcerations vs. nephrotic necrosis), and on the nature of the causative agent. An example of use of a compound of Formula I or Ia to avoid future damage is co-administration with a non-steroidal anti-inflammatory drug (for example, indomethacin).

The effective daily dosage level for compounds of Formulae I or Ia inducing cytoprotection in mammals, especially humans, will generally range from about 0.002 mg/kg to about 100 mg/kg, preferably from about 0.02 mg/kg to about 30 mg/kg. The dosage may be administered in single or divided individual doses.

Any suitable route of administration may be employed for providing a mammal, especially a human with an effective dosage of a compound of Formula I or Ia. For example, oral, rectal, transdermal, parenteral, intramuscular, intravenous and the like may be employed. Dosage forms include tablets, troches, dispersions, suspensions, solutions, capsules and the like.

The pharmaceutical compositions of the present invention comprise a compound of Formula I or Ia as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use is from about 0.01 mg to about 20 mg (preferably from about 0.1 mg to about 10 mg) of a compound of Formula I or Ia per kg of body weight per day and for cytoprotective use from about 0.002 mg to about 100 mg (preferably from about 0.02 mg to about 30 mg and more preferably from about 0.1 mg to about 10 mg) of a compound of Formula I or Ia per kg of body weight per day. In the case where an oral composition is employed, a suitable dosage range for anti-asthmatic, anti-inflammatory or anti-allergic use is, e.g. from about 1 to about 100 mg of a compound of Formula I or Ia per kg of body weight per day, preferably from about 5 mg to about 40 mg per kg and for cytoprotective use from about 0.01 mg to about 100 mg (preferably from about 0.1 mg to about 30 mg and more preferably from about 0.1 mg to about 10 mg) of a compound of Formula I or Ia per kg of body weight per day.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, a compound of Formula I or Ia can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the compounds of Formula I or Ia may also be administered by controlled release means and/or delivery devices such as those described in U.S. Pat. Nos. 3,845,770; 3,916,899; 3,536,809; 3,598,123; 3,630,200 and 4,008,719, the disclosure of which is hereby incorporated herein by reference.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms for the compounds of Formula I or Ia:

| Injectable Suspension | mg/ml |
|---|---|
| Compound of Formula I or Ia | 2.0 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |
| Tablet | mg/tablet |
| Compound of Formula I or Ia | 25.0 |
| Microcrystalline Cellulose | 325.0 |
| Providone | 14.0 |
| Microcrystalline Cellulose | 90.0 |
| Pregelatinized Starch | 43.5 |
| Magnesium Stearate | 2-2.5 |
| | 500 |
| Capsule | mg/capsule |
| Compound of Formula I or Ia | 25.0 |
| Lactose Powder | 573.5 |
| Magnesium Stearate | 1-1.5 |
| | 600 |

In addition to the compounds of Formula I or Ia, the pharmaceutical compositions of the present invention can also contain other active ingredients, such as nonsteroidal anti-inflammatory drugs (NSAIDs), peripheral analgesic agents such as zomepirac, diflunisal and the like, cyclooxygenase inhibitors, leukotriene antagonists, leukotriene biosynthesis inhibitors, H$_2$-receptor antagonists, antihistiminic agents, prostaglandin antagonists, ACE inhibitors, and thromboxane synthetase inhibitors. The weight ratio of the compound of the Formula I or Ia to the second active ingredient may be varied and will depend upon the effective dose of each ingredient. Generally, an effective dose of each will be used. Thus, for example, when a compound of the Formula I or Ia is combined with a second active ingredient the weight ratio of the compound of the Formula I or Ia to the second ingredient will generally range from about 1000:1 to about 1:1000, preferably from 200:1 to 1:200. Combinations of a compound of the Formula I or Ia and other active ingredients will generally be within the aforementioned range, but in each case, an effective dose of each active ingredient should be used.

NSAIDs can be characterized into five groups:
  (1) the propionic acid derivatives;
  (2) the acetic acid derivatives;
  (3) the fenamic acid derivatives;
  (4) the biphenylcarboxylic acid derivatives; and
  (5) the oxicams
or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structually related acetic acid derivatives having similar analgesic and antiinflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

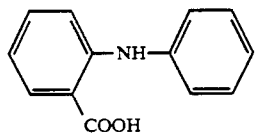

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

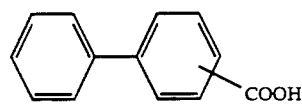

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

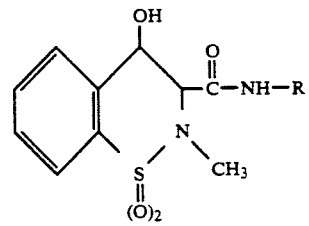

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1491, AD1590, AFP802, AFP860, AHR6293, AI77B, AP504, AU8001, BAYo8276, BPPC, BW540C, BW755C, CHINOIN 127, CN100, CO893XX, CPP, D10242, DKA9, DV17, EB382, EGYT2829, EL508, F1044, FZ, GP53633, GP650, GV3658, HG/3, ITC1, ITF, ITF182, KB1043, KC8973, KCNTEI6090, KME4, LA2851, LT696, LU20884, M7074, MED15, MG18311, MR714, MR897, MY309, NO164, ONO3144, PR823, PV102, PV108, QZ16, R830, RS2131, RU16029, RU26559, RUB265, SCR152, SH440, SIR133, SIR136, SIR92, SPAS510, SQ27239, ST281, SX1032, SY6001, SaH46798, TA60, TAI901, TEI615, TVX2706, TVX960, TZI615, U60257, UR2310, WY23205, WY41770, YM09561, YM13162, YS1033, and ZK31945.

Finally, NSAIDs which may also be used include the salicylates, specifically aspirin, and the phenylbutazones, and pharmaceutically acceptable salts thereof.

Pharmaceutical compositions comprising the Formula I or Ia compounds may also contain other inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I or Ia may also be used in combination with leukotriene antagonists such as those disclosed in EP 106,565 (Apr. 25, 1984) and EP 104,885 (Apr. 4, 1984), which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I or Ia compounds may also contain as the second active ingredient, antihistaminic agents such as benadryl, dramamine, histadyl, phenergan and the like. Alternatively, they may include other prostaglandin antagonists such as those disclosed in European Patent Application 11,067 (May 28, 1980) or other thromboxane antagonists such as those disclosed in U.S. Pat. No. 4,237,160. They may also contain histidine decarboxyase inhibitors such as α-fluoromethyl-histidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles disclosed in EP 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

When the second active ingredient in compositions of this invention is a thromboxane synthetase inhibitor, such inhibitor can be as described in UK 2,038,821 (e.g., UK 37248 and dazoxiben hydrochloride), U.S. Pat. No. 4,217,357 (e.g., UK 34787), U.S. Pat. No. 4,444,775 (e.g., CGS 13080), U.S. Pat. No. 4,226,878 (e.g., ONO 046), U.S. Pat. No. 4,495,357 (e.g., U63557A) U.S. Pat. No. 4,273,782 (e.g., UK-38485), or EP 98,690 (e.g., CV-4151).

An embodiment of the invention is a cardiovascular composition useful for treating arterial thrombosis which comprises an antithrombotic compound of the Formula I or Ia.

A further embodiment of the invention is a cardiovascular composition useful for treating arterial thrombosis which comprises: (1) the antithrombotic Formula I or Ia compound defined above; and, (ii) an angiotensin converting enzyme (ACE) inhibitor compound which is a member of the group: carboxyalkyl dipeptide derivatives; captopril [1-(3-mercapto-2-methyl-1-oxopropyl)-L-proline]; 2-[N-(S)-1-ethoxycarbonyl-3-phenylpropyl)-S-alanyl]-cis,endo-2-azabicyclo[3,3,0]octane-3(S)-carboxylic acid; N-((S)-1-ethoxycarbonyl-3-phenylpropyl)-L-alanyl-N-(2-indanyl)-glycine; 1-(N-[(S)-1-ethoxycarbonyl-3-phenylpropyl]-L-alanyl)-cis,-syn-octahydro-(H-indole-2-S)-carboxylic acid; 2-(N-[(S)-1-ethoxycarbonyl-3-phenylpropyl]-L-alanyl)-1,2,3,4-tetrahydroiso-isoquinoline-3(S)-carboxylic acid; and, 1-carboxymethyl-3(S)-(1(S)-ethoxycarbonyl-3-phenylpropylamino)-2,3,4,5-tetrahydro-1H[1]-benzazepine-2-one.

In particular the class of ACE inhibitors which have been found to have a potentiating effect when used in combination with the Formula I or Ia compounds are those disclosed in U.S. Pat. No. 4,374,829, which also discloses methods for their preparation and which patent is incorporated herein by reference and which compounds are generally represented by the Formula XI:

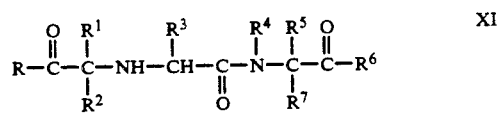

wherein
R and $R^6$ are the same or different and are hydroxy, lower $C_1$-$C_8$ alkoxy;
lower $C_1$-$C_8$ alkenoxy;
dilower $C_1$-$C_8$ alkylamino lower $C_1$-$C_8$ alkoxy (dimethylaminoethoxy);
acylamino lower $C_1$-$C_8$ alkoxy (acetylaminoethoxy);
acyloxy lower $C_1$-$C_8$ alkoxy (pivaloyloxymethoxy);
aryloxy, wherein the aryl is $C_6$ or $C_{10}$ such as phenoxy;
arlower $C_1$-$C_8$ alkoxy, such as benzyloxy;
substituted aryloxy or substituted arlower-$C_1$-$C_8$ alkoxy wherein the aryl is $C_6$ or $C_{10}$ and the substituent is methyl, halo or methoxy;
amino;
lower $C_1$-$C_8$ alkylamino;
dilower $C_1$-$C_8$ alkylamino;
hydroxyamino;
arlower $C_1$-$C_8$ alkylamino wherein the aryl group is $C_6$-$C_{10}$ such as benzylamino;
$R^1$ is hydrogen;
hydrocarbon of from 1 to 20 carbon atoms which include branched and unsaturated (such as allyl) groups;
$C_3$-$C_{10}$ cycloalkyl;
substituted lower $C_1$-$C_8$ alkyl wherein the substituent can be halo, hydroxy, lower $C_1$-$C_8$ alkoxy, aryloxy wherein the aryl is $C_6$-$C_{10}$ such as phenoxy, amino, dilower $C_1$-$C_8$ alkylamino, acylamino such as acetamido and benzamido, arylamino wherein the aryl is $C_6$ or $C_{10}$, guanidino, imidazolyl, indolyl, mercapto, lower $C_{1-8}$ alkylthio, arylthio wherein the aryl is $C_6$ or $C_{10}$ such as phenylthio, carboxy or carboxamido, carbolower $C_{1-8}$ alkoxy;
aryl of $C_6$-$C_{10}$ such as phenyl or naphthyl;
substituted aryl of $C_6$-$C_{10}$ such as phenyl wherein the substituent is lower $C_1$-$C_8$ alkyl, lower $C_1$-$C_8$ alkoxy or halo,
unsubstituted or substituted arloweralkyl, arloweralkenyl, heteroarlower alkyl, or heteroarlower alkenyl, wherein aryl groups are $C_6$ or $C_{10}$, the alkyl groups are $C_2$-$C_8$, and the heteroatoms are one of O, N or S and the substituent(s) is halo, dihalo, lower $C_1$-$C_8$ alkyl, hydroxy, lower $C_1$-$C_8$ alkoxy, amino, aminomethyl, acylamino (acetylamino or benzoylamino) dilower $C_1$-$C_8$ alkylamino, lower $C_1$-$C_8$ alkylamino, carboxyl, halolower $C_1$-$C_8$ alkyl, cyano or sulfonamido;

arlower $C_1$-$C_8$ alkyl or heteroarlower $C_1$-$C_8$ alkyl wherein the aryl group is $C_6$ or $C_{10}$ and the heteroatom is one of O, N or S, substituted on the alkyl portion by amino or acylamino (acetylamino or benzoylamino);

$R^2$ and $R^7$ are the same or different and are hydrogen or lower $C_1$-$C_8$ alkyl;

$R^3$ is hydrogen, lower $C_1$-$C_8$ alkyl, phenyl lower $C_1$-$C_8$ alkyl, aminomethyl phenyl lower $C_1$-$C_8$ alkyl, hydroxy phenyl lower $C_1$-$C_8$ alkyl, hydroxy lower $C_1$-$C_8$ alkyl, acylamino lower $C_1$-$C_8$ alkyl (such as benzoylamino lower $C_1$-$C_8$ alkyl, acetylamino lower $C_1$-$C_8$ alkyl), amino lower $C_1$-$C_8$ alkyl, dimethylamino lower $C_1$-$C_8$ alkyl, halo lower $C_1$-$C_8$ alkyl, guanidino lower $C_1$-$C_8$ alkyl, imidazolyl lower $C_1$-$C_8$ alkyl, indolyl lower $C_1$-$C_8$ alkyl, mercapto lower $C_1$-$C_8$ alkyl, lower $C_1$-$C_8$ alkyl thio lower $C_1$-$C_8$ alkyl;

$R^4$ is hydrogen or lower $C_1$-$C_8$ alkyl;

$R^5$ is hydrogen, lower $C_1$-$C_8$ alkyl, phenyl, phenyl lower $C_1$-$C_8$ alkyl, hydroxy phenyl lower $C_1$-$C_8$ alkyl, hydroxy lower $C_1$-$C_8$ alkyl, amino lower $C_1$-$C_8$ alkyl, guanidino lower $C_1$-$C_8$ alkyl, imidazolyl lower $C_1$-$C_8$ alkyl, indolyl lower $C_1$-$C_8$ alkyl, mercapto lower $C_1$-$C_8$ alkyl or lower $C_1$-$C_8$ alkyl thio lower $C_1$-$C_8$ alkyl; or, $R^4$ and $R^5$ may be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, lower $C_1$-$C_8$ alkoxy, lower $C_1$-$C_8$ alkyl or dilower $C_{1-8}$ alkyl;

and, the pharmaceutically acceptable salts thereof.

Preferred ACE inhibitor compounds of Formula XI are those wherein:

R and $R^6$ can each independently be hydroxy, lower alkoxy, lower alkenoxy, arloweralkyloxy, amino, diloweralkylamino lower alkoxy, acylamino lower alkoxy or acyloxy lower alkoxy;

$R^1$ is hydrogen,
alkyl of from 1 to 20 carbon atoms, including branched, cyclic and unsaturated alkyl groups;
substituted lower alkyl wherein the substituent is halo, hydroxy, lower alkoxy, aryloxy, amino, loweralkylamino, diloweralkylamino, acylamino, arylamino, guanidino, imidazoyl, indolyl, mercapto, loweralkylthio, arylthio, carboxy, carboxamido or carbolower alkoxy; phenyl;
substituted phenyl wherein the substituent is lower alkyl, lower alkoxy or halo;
arloweralkyl or heteroaryloweralkyl arloweralkenyl or heteroarloweralkenyl, substituted arloweralkyl, substituted heteroaryloweralkyl, substituted arloweralkenyl or substituted heteroarloweralkenyl;
wherein the substituent is halo or dihalo lower alkyl, hydroxy, lower alkoxy, amino, aminomethyl, acylamino, diloweralkylamino, loweralkylamino, carboxyl, halo alkyl, cyano or sulfonamido;
arloweralkyl or heteroarloweralkyl substituted on the alkyl portion by amino or acylamino;

$R^2$ and $R^7$ are hydrogen;

$R^3$ is lower alkyl, amino lower alkyl, imidazolyl, lower alkyl, halo lower alkyl;

$R^4$ and $R^5$ are joined to form an alkylene bridge of from 2 to 4 carbon atoms or an alkylene bridge of from 2 or 3 carbon atoms and one sulfur atom or an alkylene bridge of from 2 to 3 carbon atoms and one sulfur atom or an alkylene bridge of from 3 to 4 carbon atoms containing a double bond or an alkylene bridge of from 3 to 4 carbon atoms containing a double bond or an alkylene bridge as above substituted with hydroxy, lower alkoxy or lower alkyl;

or the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl, or thiazolyl.

More preferred are those antihypertensive compounds of Formula VI wherein:

R and $R^6$ can each independently be hydroxy, lower alkoxy, lower alkenoxy, arloweralkyloxy, amino, diloweralkylamino lower alkoxy, acylamino lower alkoxy or acyloxy lower alkoxy;

$R^1$ is alkyl having from 1-8 carbon atoms, substituted lower alkyl wherein the alkyl group has 1-5 carbon atoms and the substituent is amino, arylthio, aryloxy or arylamino, aralkyl or heteroaralkyl wherein the alkyl portion has 1-3 carbon atoms, substituted aralkyl or heteroaralkyl wherein the alkyl groups have 1-3 carbon atoms and the substituent(s) is halo, dihalo, amino, aminoalkyl, hydroxy, lower alkoxy or lower alkyl;

$R^2$ and $R^7$ are hydrogen;

$R^3$ is lower alkyl or amino lower alkyl;

$R^4$ and $R^5$ can be joined together through the carbon and nitrogen atoms to which they are attached to form a ring of the formula:

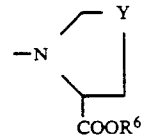

wherein Y is $CH_2$, S, or $CH-OCH_3$ or the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl.

Still more preferred antihypertensive compounds of Formula XI are those wherein: R and $R^6$ can each independently be hydroxy, lower alkoxy, aralkyloxy;

$R^2$ and $R^7$ are hydrogen;

$R^3$ is methyl, aminoloweralkyl;

$R^4$ and $R^5$ are joined through the carbon and nitrogen atoms to form proline, 4-thiaproline or 4-methoxyproline and;

$R^1$ is alkyl having from 1-8 carbon atoms, substituted lower alkyl wherein the alkyl group has 1-5 carbon atoms and the substituent is amino, arylthio or aryloxy, aralkyl or heteroaralkyl wherein the alkyl portion has 1-3 carbon atoms, substituted aralkyl or heteroaralkyl wherein the alkyl groups have 1-3 carbon atoms and the substituent(s) is halo, dihalo, amino, aminoalkyl, hydroxy, lower alkoxy or lower alkyl;

and the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl.

Examples of Formula I or Ia compounds are set forth above on pages 40-43.

Examples of Formula XI compounds are:

(i) N-(1-carboxy-3-phenylpropyl)-L-alanyl-L-proline;
(ii) N-(1-ethoxycarbonyl-3-phenylpropyl)-L-alanyl-L-proline;
(iii) N-(1-ethoxycarbonyl-4-methylpentyl)-L-alanyl-L-proline;
(iv) N-(1-carboxy-5-aminopentyl)-L-alanyl-L-proline;
(v) N-α-(1-carboxy-3-phenylpropyl)-L-lysyl-L-proline;
(vi) N-α-(1-ethoxycarbonyl-3-phenylpropyl)-L-lysyl-L-proline;
(vii) N-α-[1-carboxy-3-(3-indolyl)-propyl]-L-lysyl-L-proline;
(viii) N-α-[1-carboxy-3-(4-chlorophenyl)-propyl]-L-lysyl-L-proline;
(ix) N-α-[1-carboxy-2-phenylthioethyl]-L-lysyl-L-proline;
(x) N-α-[1-carboxy-3-(4-chlorophenyl)-propyl]-L-lysyl-trans-4-methoxy-L-proline;
(xi) N-α-[1-carboxy-5-aminopentyl]-L-lysyl-L-proline;
(xii) N-α-(1-carboxy-3-phenylpropyl)-L-ornithyl-L-proline;
(xiii) ethyl N-(1-ethoxycarbonyl-3-phenylpropyl)-L-alanyl-L-prolinate hydrochloride;
(xiv) N-[1-(ethoxycarbonyl)-3-(4-imidazolyl)propyl]-L-alanyl-L-proline.
(xv) N-[1-carboxy-3-(4-imidazolyl)propyl]-L-lysyl-L-proline;
(xvi) N-(1(S)-carboxy-3-phenylpropyl)-L-alanyl-L-proline;
(xvii) N-(1(S)-ethoxycarbonyl-3-phenylpropyl)-L-alanyl-L-proline maleate salt;
(xviii) N-α-(1(S)-carboxy-3-phenylpropyl)-L-lysyl-L-proline;
(xix) ethyl N-(1(S)-ethoxycarbonyl-3-phenylpropyl)-L-alanyl-L-prolinate hydrochloride;
(xx) N-α-(1(S)-ethoxycarbonyl-3-phenylpropyl)-L-lysyl-L-proline.

The above-described Formula VI compounds, their use and the method of preparation thereof are disclosed in U.S. Pat. No. 4,374,829 the disclosure of which is hereby incorporated herein by reference.

The resolution of certain Formula I and Ia compounds into their optically pure enantiomers is as disclosed in U.S. Pat. Nos. 4,424,355 and 4,435,579 which have been incorporated herein by reference.

The combination composition of the invention can contain varying amounts of the Formula I or Ia (i) anti-thrombotic compound and Formula VI (ii) antihypertensive compounds. The weight ratio of (i):(ii) can range from about 25 to 1; preferably from about 10 to 1. In addition to the active ingredients of (i) alone or of (i) and (ii) in combination, the compositions of the invention can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the present composition.

The combination compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration. These compositions are formulated similarly to the compositions discussed on pages 46 to 51, above.

Treatment dosage for human beings for cardiovascular use can be varied as necessary. Generally, daily dosages of the composition of the invention can range from about 6000 to about 10 mg; preferably, from about 3000 to about 20 mg.

The amount of active ingredient that may be combined with the carrier materials to produce a single dosage form for cardiovascular use will vary depending upon the host treated and the particular mode of administration. For example, a formulation intended for oral administration may contain from 5 mg to 5 gm of active agents compounded with an appropriate and convenient amount of carrier material which may vary from about 5 to about 95 percent of the total composition. Dosage unit forms will generally contain between from about 20 mg to about 500 mg of active ingredients.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The composition of this invention inhibits platelet accumulation at the damaged endothelial surface via the Formula I or Ia compound. This inhibitory effect is potentiated by the presence of the antihypertensive compound.

Thus, the compositions of the invention are useful in treating thrombosis and are also of value in the management of acute and chronic congestive heart failure.

In vivo testing of the composition of this invention in test animals (rabbits) can be used to demonstrate that this composition is pharmaceutically effective in decreasing platelet-related arterial thrombic formation.

To demonstrate the potentiation of the antihypertensive compound on the anti-thrombotic Formula I or Ia compound comprising the combination composition of the invention, the effect of these compounds on test animals (rabbits) can be determined separately and then in combination. The effect of a different class of antihypertensive agents singly and in combination with the Formula I or Ia compound of the invention can also be determined for comparative purposes. The methods employed are described in a copending application, attorney docket no. 17062, U.S. Ser. No. 617,293, filed June 4, 1984, which is hereby incorporated herein by reference.

The following examples illustrate the preparation of the compounds of the present invention without, however, limiting the same thereto.

All temperatures are in degrees Celsius.

EXAMPLE 1

A. Preparation of Hydrazine Starting Materials
1-[(4-Chlorophenyl)methyl]-1-(4-methylphenyl)hydrazine A mixture of 10 g of p-tolylhydrazine hydrochloride, 75 ml of toluene and 11.5 ml of triethylamine was heated at reflux for 60 minutes. Then, 7.1 g of p-chlorobenzyl chloride was added. After stirring 16 hours at reflux, triethylamine hydrochloride was filtered off and washed with ethyl ether. The filtrate and washing were concentrated in vacuo and chromatographed on a silica gel column (hexane-ethylacetate, 9:1) to give 6.64 g of the title compound, (Compound No. 5 in Table 3).

Other hydrazines, similarly prepared, are also shown in Table 3.

TABLE 3

Hydrazines

| Compound No. | X | Y | Compound Name |
|---|---|---|---|
| 1. | 4-F | Cl | 1-[(4-chlorophenyl)-methyl]-1-(4-fluorophenyl)hydrazine hydrochloride |
| 2. | 3,5-Cl$_2$ | Cl | 1-[(4-chlorophenyl)-methyl]-1-(3,5-dichlorophenyl)hydrazine hydrochloride |
| 3. | 3-OMe | Cl | 1-[(4-chlorophenyl)-methyl]-1-(3-methoxyphenyl)hydrazine hydrochloride |
| 4. | 3-Me | Cl | 1-[(4-chlorophenyl)-methyl]-1-(3-methylphenyl)hydrazine hydrochloride |
| 5. | 4-Me | Cl | 1-[(4-chlorophenyl)-methyl]-1-(4-methylphenyl)hydrazine hydrochloride |
| 6. | 4-Cl | Cl | 1-[(4-chlorophenyl)-methyl]-1-(4-chlorophenyl)hydrazine hydrochloride |
| 7. | H | Cl | 1-[(4-chlorophenyl)-methyl]-1-(phenyl)hydrazine hydrochloride |
| 8. | 4-Br | Cl | 1-[(4-chlorophenyl)-methyl]-1-(4-bromophenyl)hydrazine hydrochloride |
| 9. | 4-OMe | SMe | 1-[(4-methylthiophenyl)-methyl]-1-(4-methoxyphenyl)hydrazine hydrochloride |
| 10. | 4-OMe | Cl | 1-[(4-chlorophenyl)-methyl]-1-(4-methoxyphenyl)hydrazine hydrochloride |
| 11. | 4-OMe | NO$_2$ | 1-[(4-nitrophenyl)-methyl]-1-(4-methoxyphenyl)hydrazine hydrochloride |
| 12. | 4-F | SMe | 1-[(4-methylthiophenyl)-methyl]-1-(4-fluorophenyl)hydrazine hydrochloride |

EXAMPLE 2

3 (or Beta)-[1-(p-Chlorobenzyl)-5-chloro-3-methyl-2-indolyl]-propionic acid

Step 1

To 1.84 g of 1,1-[(4-chlorophenyl)methyl]-1-(4-chlorophenyl) hydrazide hydrochloride in 60 cc of tert-butanol was added 868 mg of methyl 4-oxo-hexanoate. The reaction mixture was refluxed under nitrogen for 16 hours. The resulting reaction mixture was then evaporated to dryness and the resulting residue suspended in CH$_2$Cl$_2$. The solid material was then filtered. The filtrate was washed with water, dried and evaporated. The resulting syrup was then chromatographed on silica gel to give 1.47 g of indole derivative (65%).

NMR: H$^1$ NMR (CDCl$_3$): 2.25 ppm (Me, 3H, singlet); 2.43 (CH$_2$, 2H, triplet); 3.01 (CH$_2$, 2H, triplet); 3.64

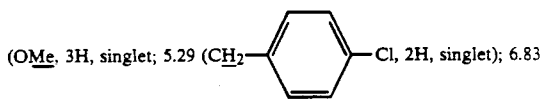

(OMe, 3H, singlet; 5.29 (CH$_2$—⟨ ⟩—Cl, 2H, singlet); 6.83

(H-2' and H-6', 2H, d); 7.1 (H-6, and H-7, 2H, multiplet); 7.25 (H-3' and H-5', 2H); 7.49 (H-4, 1H, singlet).

Step 2

To 1.06 g of methyl ester in 350 ml of EtOH was added 169 mg of sodium hydroxide dissolved in 3 ml of H$_2$O. The resulting solution was stirred at room temperature for 16 hours. The reaction mixture was then acidified with HCl (1N) and concentrated. The resulting solution was then extracted with CH$_2$Cl$_2$ (3 times). The combined organic layer was washed with brine, dried over MgSO$_4$, and evaporated to give 1 g of solid material (100% yield). An analytical sample of this material was be prepared by triturating the resulting solid material with hexane followed by a filtration (800 mg).

Analysis calculated for C$_{19}$H$_{17}$Cl$_2$NO$_2$: C, 62.99; H, 4.74; N, 19.58. Found: C, 63.19; H, 4.78; N, 19.35.

EXAMPLE 3

3 (or Beta)-[1-(p-Chlorobenzyl)-3-methyl-5-fluoro-2-indolyl]-propionic acid

Following the procedure of Example 2, but using 1-[(4-chlorophenyl)methyl]-1-(4-fluorophenyl)-hydrazine hydrochloride and methyl 4-oxohexanoate as the starting materials and ethanol as the solvent, the title compound was prepared.

Analysis calculated for C$_{19}$H$_{17}$ClFNO$_2$: C, 65.98; H, 4.95; Cl, 10.25. Found: C, 65.56; H, 5.17; Cl, 10.52.

EXAMPLE 4

3 (or Beta)-[1-p-Chlorobenzyl-3-methyl-4,6-dichloro-2-indolyl]propionic acid Following the procedure of Example 2, but using 1-[(4-chlorophenyl)methyl]-1-(3,5-dichlorophenyl)hydrazine hydrochloride and methyl 4-oxohexanoate as the starting materials and ethanol as the solvent, the title compound was prepared.

Analysis calculated for C$_{19}$H$_{16}$O$_2$Cl$_3$N: C, 57.52; H, 4.06. Found: C, 57.40; H, 4.20.

EXAMPLE 5

3 (or Beta)-[1-(p-Chlorobenzyl)-3-methyl-4-methoxy-2-indolyl]propionic acid

Following the procedure of Example 2, but using 1-[(4-chlorophenyl)methyl]-1-(3-methoxyphenyl)-hydrazine hydrochloride and ethyl 4-oxohexanoate as the starting materials and ethanol as the solvent, the title compound was prepared.

Analysis calculated for $C_{20}H_{20}O_3NCl$: C, 67.12; H, 5.63. Found: C, 67.40; H, 5.43.

EXAMPLE 6

3 (or Beta)-[1-(p-chlorobenzyl)-3-methyl-6-methoxy-2-indolyl]propionic acid

Following the procedure of Example 2, but using 1-[(4-chlorophenyl)methyl]-1-(5-methoxyphenyl)-hydrazine hydrochloride and methyl 4-oxohexanoate as the starting materials and tert-butanol as the solvent, the title compound was prepared.

Analysis calculated for $C_{20}H_{20}O_3NCl$: C, 67.12; H, 5.63; N, 3.91; Cl, 9.90. Found: C, 67.08; H, 5.64; N, 4.09.

EXAMPLE 7

3 (or Beta)-[1-(p-Chlorobenzyl)-3,4-dimethyl-2-indolylpropionic acid and 3 (or Beta)-[1-(p-chlorobenzyl)-3,6-dimethyl-2-indolyl]propionic acid (as a mixture)

Following the procedure of Example 2, but using 1-[(4-chlorophenyl)methyl]-1-(3-methylphenyl)-hydrazine hydrochloride and methyl 4-oxohexanoate as the starting materials and t-butanol as the solvent, the title compounds were prepared.

Analysis calculated for $C_{20}H_{20}NClO_2$: C, 70.26; H, 5.89; N, 40.9; Cl, 10.37. Found: C, 70.52; H, 5.57; N, 4.56; Cl, 10.03.

EXAMPLE 8

1-(4-Chlorobenzyl)-3-methyl-5-methoxy-2-(4'-carboxybutyl)indole

Following the procedure of Example 2, but using 1-[(4-chlorophenyl)methyl]-1-(4-methoxyphenyl)-hydrazine hydrochloride and methyl 6-oxooctanoate as the starting materials and methanol as the solvent, the title compound was prepared.

Analysis calculated for $C_{22}H_{24}NO_3Cl$: C, 68.57; H, 6.23; N, 3.63. Found: C, 68.45; H, 6.41; N, 3.35.

EXAMPLE 9

3 (or Beta)-[1-(p-Chlorobenzyl)-3,5-dimethyl-2-indolyl]propionic acid

Following the procedure of Example 2, but using 1-[(4-chlorophenyl)methyl]-1-(4-methylphenyl)-hydrazine hydrochloride and methyl 4-oxohexanoate as the reactants and ethanol as the solvent, the title compound was prepared.

Analysis calculated for $C_{20}H_{20}O_2NCl$: C, 70.31; H, 5.90; N, 4.1; Cl, 10.37. Found: C, 70.37; H, 5.85; N, 4.10; Cl, 10.15.

EXAMPLE 10

1-(4-Chlorobenzyl)-3-methyl-5-methoxy-2-(3-carboxypropyl)indole

Following the procedure of Example 2, but using 1-[(4-chlorophenyl)methyl]-1-(4-methoxyphenyl)hydrazine hydrochloride and methyl 5-oxoheptanoate as the starting materials and ethanol as the solvent, the title compound was prepared.

Analysis calculated for $C_{21}H_{22}NO_3Cl$: C, 67.83; H, 5.92; N, 3.76. Found: C, 67.92; H, 5.97; N, 3.84.

EXAMPLE 11

3 (or Beta)-[1-(p-Chlorobenzyl)-3-methyl-2-indolyl]-propionic acid

Following the procedure of Example 2, but using 1-[(4-chlorophenyl)methyl]-1-(phenyl)hydrazine hydrochloride and methyl 4-oxohexanoate as the starting materials and tert-butanol as the solvent, the title compound was prepared.

Analysis calculated for $C_{19}H_{18}O_2ClN$: C, 67.15; H, 5.33; N, 4.12; Cl, 10.43. Found: C, 67.77; H, 5.42; N, 4.48; Cl, 10.48.

EXAMPLE 12

3 (or Beta)-[1-(p-Chlorobenzyl)-5-bromo-3-methyl-2-indolyl]propionic acid

Following the procedure of Example 2, but using 1-[(4-chlorophenyl)methyl]-1-(4-bromophenyl)-hydrazine hydrochloride and methyl 4-oxohexanoate as the starting materials and t-butanol as the solvent, the title compound was prepared.

Analysis calculated for $C_{19}H_{17}ClO_2BrN$: C, 56.10; H, 4.21; Found: C, 56.07; H, 4.27.

EXAMPLE 13

1-(4-Thiomethylbenzyl)-5-methoxy-3-methyl-2-(2-carboxyethyl)indole

Following the procedure of Example 2, but using 1-[(4-methylthiophenyl)methyl]-1-(4-methoxyphenyl)-hydrazine hydrochloride and methyl 4-oxohexanoate as the starting materials and tert-butanol as the solvent, the title compound was prepared.

Analysis calculated for $C_{21}H_{23}NO_3S$: C, 68.29; H, 6.23; N, 3.79. Found: C, 68.03; H, 6.12; N, 3.76.

EXAMPLE 14

1-(4-Thiomethylbenzyl)-5-methoxy-3-methyl-2-(2-carboxyethyl)indole S-oxide

Using the methyl ester of the title compound of Example 13 as the starting material, 250 mg were dissolved in 20 ml of dichloro methane and cooled to 0° C. Meta-chloroperoxybenzoic acid, 138 mg, was added and the reaction stirred at 0° C. for 1 hour. 200 mg anhydrous $Ca(OH)_2$ was added and the reaction filtered and evaporated to dryness. The methyl ester so obtained was hydrolyzed according to the conditions described in Example 2.

Analysis calculated for $C_{21}H_{23}NO_4S$: C, 63.45; H, 5.70; N, 3.47. Found: C, 63.55; H, 5.67; N, 3.32.

EXAMPLE 15

1-(4-Thiomethylbenzyl)-5-methoxy-3-methyl-2-(3-carboxypropyl)indole

Following the method of Example 2, but using 1-[(4-methylthiophenyl)methyl]-1-(4-methoxyphenyl)-hydrazine hydrochloride and methyl 4-oxoheptanoate as the starting materials and tert-butanol as the solvent, the title compound was prepared.

Analysis calculated for $C_{22}H_{25}NO_3S\cdot\frac{1}{2}H_2O$: C, 67.86; H, 6.64; N, 3.50. Found: C, 66.85; H, 6.63; N, 3.31.

EXAMPLE 16

4-[1-(p-Chlorobenzyl)-3-methyl-5-fluoro-2-indolyl]-butanoic acid

Following the method of Example 2, but using 1-[(4-chlorophenyl)methyl]-1-(4-fluorophenyl)hydrazine hydrochloride and methyl 5-oxoheptanoate as the starting materials and tert-butanol as the solvent, the title compound was prepared.

Analysis calculated for $C_{20}H_{19}ClFNO_2$: C, 66.76; H, 5.32; Cl, 9.85. Found: C, 66.89; H, 5.24; Cl, 10.26.

EXAMPLE 17

3 (or Beta)-[1-(p-Thiomethylbenzyl)-3-methyl-5-fluoro-2-indolyl]propanoic acid

Following the procedure of Example 2, but using 1-[(4-methylthiophenyl)methyl]-1-(4-fluorophenyl)hydrazine hydrochloride and methyl 4-oxohexanoate as the starting materials and tert-butanol as the solvent, the title compound was prepared.

Analysis calculated for $C_{20}H_{20}O_2FSN$: C, 67.20; H, 5.64; N, 3.91. Found: C, 67.21; H, 5.91; N, 3.88.

EXAMPLE 18

3 (or Beta)-[1-p-Methylsulfoxylbenzyl)-3-methyl-5-fluoro-2-indolyl]-propanoic acid Using the title compound of Example 17, treated according to the procedure described in Example 14, the title compound was obtained.

Analysis calculated for $C_{20}H_{20}FNO_3S$: C, 64.32; H, 5.39; N, 3.75. Found: C, 64.18; H, 5.65; N, 3.48.

EXAMPLE 19

3-[1-(4-Chlorobenzyl)-3-methyl-5-methoxy-2-indolyl]-butanoic acid

Following the method of Example 2, but using 1-[(4-chlorophenyl)methyl]-1-(4-methoxyphenyl)-hydrazine hydrochloride and methyl 3-methyl-4-oxohexanoate as the starting materials and methanol as the solvent, the title compound was prepared.

Analysis calculated for $C_{21}H_{22}NO_3Cl\cdot H_2O$: C, 64.78; H, 6.13; N, 3.59. Found: C, 65.86; H, 6.12; N, 3.37.

EXAMPLE 20

3-Methyl-4-[1-p-chlorobenzyl-5-methoxy-3-methylindol-2-yl]butanoic acid

Following the method of Example 2, but using 1-[(4-chlorophenyl)methyl]-1-(4-methoxyphenyl)hydrazine hydrochloride and 3-methyl-5-oxoheptanoic acid as the starting materials and isopropanol as the solvent, the title compound was prepared.

Analysis calculated for $C_{22}H_{24}O_3NCl$: C, 68.48; H, 6.27; N, 3.63; Cl, 9.19. Found: C, 68.49; H, 6.50; N, 3.55; Cl, 8.93.

EXAMPLE 21

3-Methyl-4-[1-p-chlorobenzyl-5-fluoro-3-methylindol-2-yl]butanoic acid

Following the method of Example 2, but using 1-[(4-chlorophenyl)methyl]-1-(4-fluorophenyl)hydrazine hydrochloride and 3-methyl-4-oxoheptanoic acid as the starting materials and isopropanol as the solvent, the title compound was prepared.

Analysis calculated for $C_{21}H_{21}O_2NClF$: Calc.: C, 67.47; H, 5.66; N, 3.75; Cl, 9.48; F, 5.08. Found: C, 67.57; H, 5.90; N, 3.60; Cl, 9.44; F, 4.50.

EXAMPLE 22

3-(1-p-Chlorobenzyl-3-methyl-5-methoxyindol-2-yl)-2,2-dimethylpropanoic acid

Following the method of Example 2, but using 1-[(4-chlorophenyl)methyl]-1-(4-methoxyphenyl)hydrazine hydrochloride and methyl 2,2-dimethyl-4-oxohexanoate as the starting materials and tert-butanol as the solvent, the title compound was prepared.

Analysis calculated for $C_{22}H_{24}NO_3Cl$: Calc.: C, 64.48; H, 6.40; N, 3.63. Found: C, 68.32; H, 6.37; N, 3.53.

EXAMPLE 23

3-[1-p-Chlorobenzyl-5-hydroxy-3-methylindol-2-yl]-propionic acid

Beginning with 3-[1-p-chlorobenzyl-5-methoxy-3-methylindol-2-yl]propionic acid which is described in J. Med. Chem., 1252 (1968), (2.7 g) was dissolved in 20 ml $CH_2Cl_2$ at 0° C. 7.6 ml $BBr_3$ (1M in $CH_2Cl_2$) was added dropwise and the reaction stirred for 60 minutes. After 180 minutes at 23° C., another 4 ml $BBr_3$ solution was added. The reaction was stirred for a further 180 minutes. The reaction was cooled to $-20°$ C. and 15 ml MeOH added. The organic phase was washed with $NaHCO_3$ (aqueous), dried with $Na_2SO_4$ and chromatographed on silica gel. Hydrolysis of the methyl ester was carried out as described in Example 2 to yield 2.2 g of the title compound.

Analysis calculated for $C_{19}H_{18}O_3ClN$: C, 66.37; H, 5.27; N, 4.07; Cl, 10.31. Found: C, 66.54; H, 5.16; N, 3.85; Cl, 10.65.

EXAMPLE 24

3-[1-p-Chlorobenzyl-5-acetoxy-3-methylindol-2-yl]-propionic acid

Using the title compound of Example 23 as starting material, (1 g) was dissolved in $CH_2Cl_2$ (20 ml) at 0° C. and 1 ml pyridine added. 1.8 g acetic anhydride was added and the reaction let stir at 23° for 16 hours. The organic phase was washed with $H_2O$ (5×5 ml), evaporated and chromatographed.

Analysis calculated for $C_{21}H_{20}O_3NCl$: Calc.: C, 65.37; H, 5.22; N, 3.63; Cl, 9.19. Found: C, 65.35; H, 5.09; N, 3.54; Cl, 9.25.

EXAMPLE 25

3-[4,6-dichloro-1-(4-chlorobenzyl)-3-methyl-1H-indol-2-yl] propanoic acid

Following the method of Example 2, but using 1-[1-(chlorophenyl)methyl-1-(3,5-dichlorophenyl) hydrazine hydrochloride and methyl 4-oxohexanoate as the starting materials, in t-butanol as solvent, the title compound was prepared.

| Analysis calculated for $C_{19}H_{16}NCl_3O_2$ | | |
|---|---|---|
| C | H | |
| 57.52 | 4.06 | Calc. |
| 57.40 | 4.20 | Found |

EXAMPLE 26

3-[1-(4-chlorobenzyl)-4-methoxy-3-methyl-1H-indol-2-yl] propanoic acid

Following the method of Example 2, but using 1-[4-(chlorobenzyl)-1-(3-methoxy phenyl) hydrazine hydrochloride and methyl-4-oxohexanoate as the starting materials in t-butanol as solvent, the title compound was prepared, m.p. 145° C.

Analysis calculated for $C_{20}H_{20}O_3NCl$: Calc.: C, 67.12; H, 5.63. Found: C, 67.40; H, 5.43.

EXAMPLE 27

1-[1-(4-chlorobenzyl)-3-methyl-5-fluoroindol-2-yl]-methoxy acetic acid

Step 1

Methyl 1-(4-chlorobenzyl)-5-fluoro-3-methylindol-2-carboxylate

Following the procedure of Example 42 Step 1, but using 1-(4-chlorobenzyl)-1-(4-fluorophenyl)-hydrazine in place of 1-(4-chlorobenzyl)-1-(4-methoxyphenyl)hydrazine, there was obtained the title compound of Step 1.

Step 2

1-[1-(4-chlorobenzyl)-3-methyl-5-fluoroindol-2-yl]methanol 1.50 g 1-(4-chlorobenzyl)-3-methyl-5-fluoro-1H-indole-2-carboxylate Me ester was dissolved in 50 ml dry THF. Diisobutyl aluminum hydride (1.5M) in tetrahydrofuran (THF) (2 equivalents) was added at −78° C. The reaction was stirred for 16 hrs., allowed to reach room temperature and quenched with NH$_4$Cl (aq.). The organic phase was separated, dried (Na$_2$SO$_4$) and evaporated to produce 1.32 g of product which was purified on column chromatography to yield the title compound of Step 2.

Step 3

The title compound from Step 2 (1.0 g) was dissolved in dry dimethylformamide (DMF) (10 ml) at −20° C. Potassium hexamethyl disilazane base in toluene (0.69M) was added (1.1 molar equivalents) and the reaction stored for 1 hr. Ethyl 2-bromo acetate (580 mg) (1.2 equivalents) was added and the reaction stirred for 16 h at 21° C. Water was added (3 ml). The product was isolated after extraction from the aqueous DMF with ether. Following purification on column chromatography, the title ethyl ester was hydrolysed in 3N NaOH according to the procedure in Example 2.

M.P. = 154°

EXAMPLE 28

3-[1-(4-bromobenzyl)-3-methyl-5-methoxyindol-2-yl]-2,2-dimethylpropanoic acid

Following the method of Example 2, but using 1-[4-bromobenzyl]-1-(4-methoxy phenyl) hydrazine hydrochloride and methyl-2,2-dimethyl-4-oxohexanoate as the starting materials, using t-butanol as the solvent, the title compound was prepared.

M.P. = 170°

EXAMPLE 29

3-[1-(4-chlorobenzyl)-3-methyl-5-methoxyindol-2-yl]2-methyl propanoic acid

Following the method of Example 2, but using 1-[4-chlorobenzyl]-1-(4-chlorophenyl) hydrazine hydrochloride and methyl-3-methyl-4-oxohexanoate as starting materials, using t-butanol as solvent, the title compound was prepared.

M.P. = 128°

EXAMPLE 30

3-[1-(4-iodobenzyl)-3-methyl-5-methoxyindol-2-yl]-2,2-dimethyl propanoic acid

Following the method of Example 2, but using 1-[4-iodobenzyl]-1-(4-methoxyphenyl)hydrazine hydrochloride and methyl-2,2-dimethyl-4-oxo-hexanoate as starting materials, using t-butanol as solvent, the title compound was prepared.

M.P. = 152°

EXAMPLE 31

3-[1-(4-chlorobenzyl)-3-methyl-5-methoxyindol-2-yl]-2,2-dimethyl propanol 700 mg of 3-[1-(4-chlorobenzyl)-3-methyl-5-methoxyindol-2-yl]-2,2-dimethyl propanoic acid methy ester was dissolved in 20 ml dry tetrahydrofuran. The reaction was cooled to −78° C. and 2 equivalents di-isobutyl aluminium hydride (DIBAL) in THF was added. The reaction was allowed to warm to room temperature and quenched with NH$_4$Cl (aq.). Ethyl acetate was added (75 ml) and the organic phase separated, dried and evaporated. The product was isolated by column chromatography.

M.P. = 100.1°

EXAMPLE 32

3-[1-(4-chlorobenzyl)-3-methoxy-5-hydroxyindol-2-yl]-2,2-dimethyl propanoic acid Following the method of Example 23, but using the product of Example 22 as starting material, the title compound was prepared.

M.P. = 137°

EXAMPLE 33

3-[1-(4-chlorobenzyl)-3-methyl-5-methoxyindol-2-yl]-propanol

Following the method of Example 31, but using the starting material of Example 23, the title compound was prepared.

M.P. = 118°

EXAMPLE 34

3-[1-(4-chlorobenzyl)-3-methyl-5-fluoroindol-2-yl]-2,2-dimethyl propanoic acid

Following the method of Example 2, but using 1-[4-chlorobenzyl]-1-(4-fluorophenyl)hydrazine hydrochloride 1.9 g and 2,2-dimethyl-4-oxohexanoic acid (950 mg) as starting materials, in t-butanol as solvent, after 16 hrs. at reflux, the solvent was removed in vacuo, and the title compound was isolated by crystallization and filtration, followed by crystallization from hot ethyl acetate:hexane 9:1.

| Analysis for $C_{21}H_{21}NO_2ClF$ | | |
| --- | --- | --- |
| C | H | |
| 67.47 | 5.62 | Calc. |
| 67.53 | 5.70 | Found |

M.P.=124°

EXAMPLE 35

3-[1-(4-chlorobenzyl)-3-methyl-5-fluoroindol-2-yl]-3-methyl propanoic acid

Following the method of Example 2, but using 1-[4-chlorobenzyl]-1-(4-fluorophenyl) hydrazine hydrochloride and methyl 3-methyl-4-oxohexanoate as starting materials, the title compound was prepared.
M.P.=143°

EXAMPLE 36

3-[1-(4-chlorobenzyl)-3-methyl-5-hydroxyindol-2-yl]butanoic acid

Following the method of Example 23, but using the product of Example 19 as starting material, the title compound was prepared.
M.P.=162°

EXAMPLE 37

Methyl 4-[1-(4-chlorobenzyl)-3-methyl-5-fluoroindol-2-yl]-butanoate

Following the method of Example 44, but using the product of Example 16 as starting materials, the title compound was prepared.

| Analysis for $C_{21}H_{21}NO_2FCl$ | | |
| --- | --- | --- |
| C | H | |
| 67.47 | 5.62 | Calc. |
| 67.53 | 5.70 | Found |

EXAMPLE 38

3-[1-(4-chlorobenzyl)-3-methyl-4-propyl-5-hydroxyindol-2-yl]-propanoic acid 210 mg of the methyl ester of Example 39 was heated in a Kugelrohr vacuum distillation apparatus at 200° C. without vacuum for 90 min. The product was then distilled in vacuo at 0.1 mm Hg, 200° C. The liquid obtained was chromatographed on a preparative plate (hexane 8, ethyl acetate 2). 125 mg. of 3-[1-(4-chlorobenzyl)-3-methyl-4-(3-propyl)-5-hydroxyindol-2-yl]propanoic acid methyl ester was isolated, which was then hydrogenated with 10% palladium on charcoal in 10 ml of MeOH with 40 psi $H_2$ for 3 min. The methyl ester title compound was isolated from a preparative plate ($SiO_2$) (hexane 8, ethyl acetate 2) (82 mg) and the corresponding acid was obtained from hydrolysis as shown in Example 2.

| Analysis calculated for $C_{22}H_{24}O_3NCl + 2H_2O$ | | |
| --- | --- | --- |
| C | H | |
| 62.43 | 6.06 | Calc. |
| 62.62 | 5.73 | Found |

EXAMPLE 39

3-[1-(4-chlorobenzyl)-3-methyl-5-prop-2-enoxyindol-2-yl]-propanoic acid

Using 845 mg of the product of Example 23 as starting material, diluted in 23 ml of dimethyl ketone, 476 mg of potassium carbonate and 225 μl of allyl bromine was added. The reaction was refluxed overnight. The reaction was then diluted with water and the acetone removed in vacuo. Then the reaction was extracted with $CH_3CO_2Et$ and the organic phase was dried and concentrated to yield after flash chromatography (hexane 8, ethyl acetate 2) 790 mg of the compound, which was then hydrolyzed following the procedure of Example 2.

| Analysis calculated for $C_{22}H_{22}O_3NCl$ | | |
| --- | --- | --- |
| C | H | |
| 68.83 | 5.77 | Calc. |
| 68.88 | 5.89 | Found |

M.P.=131.2°

EXAMPLE 40

Methyl-3-[1-(4-chlorobenzyl-3-methyl-5-methoxyindol-2-yl]-2,2-dimethyl-propanoate Following the method of Example 45, but using the product of Example 22 as starting material, the title compound was prepared.
M.P.=110°

EXAMPLE 41

3-[1-(4-chlorobenzyl)-3-methyl-5-fluoroindol-2-yl]-2-methyl-butanoic acid

Step 1

Ethyl 2,3-dimethyl-4-oxo-hexanoate

To 4.23 g ethyl 2-bromopropionate in 50 ml acetonitrile was added 2.5 g N-[3-(pent-2-enyl)]-pyrrolidine. The reaction was refluxed for 16 hr. The solvent was removed in vacuo and the product was isolated by chromatography on silica gel to yield 1.5 g of the title compound which was used as such in the second step.

Step 2

Following the method of Example 2, but using 1-[4-chlorobenzyl]-1-(4-fluorophenyl) hydrazine hydrochloride and ethyl 2,3-dimethyl-4-oxohexanoate as starting materials, the title compound was prepared.
M.P.=177°

EXAMPLE 42

1-(4-chlorobenzyl)-3-methyl-5-methoxy-1H-indole-2-methoxy acetic acid.

Step 1

Methyl 1-(4-chlorobenzyl)-5-methoxy-3-methylindol-2-carboxylate

To a solution of 1 g 2-keto butyric acid in 35 ml MeOH (to which had previously been added 1 ml $CH_3COCl$ at 0° C.) was added 12.82 g N-benzyl-4-methoxyphenyl hydrazine hydrochloride. The solution was refluxed for 1 hr., the methanol distilled off and a crystalline pasty residue triturated with methanol to give 2.6 g crystalline material. The crystals were swished with 9:1 hexane:EtOAc overnight to yield 2.0 g pure product, which was used as such in the next step.

Step 2

1-(4-chlorobenzyl)-3-methyl-5-methoxy-1H-indole-2-methanol.

1.50 g 1-(4-chlorobenzyl)-3-methyl-5-methoxy-1H-indole-2-carboxylate methyl ester was dissolved in 50 ml dry THF. Diisobutyl aluminum hydride (1.5M) in THF (2 equivalents) was added at −78° C. The reaction was stirred for 16 hrs., allowed to reach room temperature and quenched with $NH_4Cl$ (aq.). The organic phase was separated, dried ($Na_2SO_4$) and evaporated to produce 1.32 g of product which was purified on column chromatography to yield the title compound of Step 2.

Step 3

The product from Step 2 above (1.0 g) was dissolved in dry DMF (10 ml) at −20° C. Potassium hexamethyl disilazane base in toluene (0.69M) was added (1.1 molar equivalents) and the reaction stirred for 1 hr. Ethyl 2-bromo acetate (580 mg)=1.2 equivalents was added and the reaction stirred for 16 h at 21° C. Water was added (3 ml). The product was isolated after extraction from the aqueous DMF with ether. Following purification on column chromatography, the title ethyl ester was hydrolysed in 3N NaOH according to the procedure in Example 2.

M.P.=128°

EXAMPLE 43

3-[1-(4-chlorobenzyl)-3-methyl-5-chloroindol-2-yl]-2,2-dimethyl-propanoic acid

Following the method of Example 2, but using 1-[4-chlorobenzyl]-1-[4-chlorophenyl]hydrazine hydrochloride and methyl-2,2-dimethyl-4-oxohexanoate in t-butanol as solvent, the title compound was prepared.

M.P.=142.5°

EXAMPLE 44

Methyl-3-[-1-(4-chlorobenzyl)-5-methoxy-3-methyl-1H-indol-2-yl]propanoate

3-[1-(4-chlorobenzyl)-5-methoxy-3-methyl-1H-indol-2-yl]propanoic acid (50 g) was dissolved in 400 ml absolute methanol and cooled to 0° C. Boron trifluoride etherate (50 ml) was added slowly over 25 min. The reaction was quenched after 16 hr. by the addition of water/$NaHCO_3$. Upon evaporation, the water was removed by extraction with $CH_2Cl_2$. The organic phase was dried and concentrated to yield 47 g of the title methyl ester.

| Analysis calculated for $C_{20}H_{21}NO_3Cl$: | | | | |
| --- | --- | --- | --- | --- |
| | C | H | N | Cl |
| Calc.: | 67.83 | 5.96 | 3.77 | 9.53 |
| Found: | 67.67 | 5.21 | 3.68 | 9.68 |

EXAMPLE 45

3-[1-(4-aminobenzyl)-5-methoxy-3-methyl-1H-indol-2-yl]-2,2-dimethyl propanoic acid

Step 1

3-[1-(4-nitrobenzyl)-5-methoxy-3-methyl-1H-indol-2-yl]-2,2-dimethyl propanoic acid Following the method of Example 2, but using 1-[(4-nitrophenyl)methyl-1-(4-methoxyphenyl) hydrazine hydrochloride and methyl 2,2-dimethyl-4-oxo-hexanoate as the starting materials and tert-butanol as the solvent, the title compound was prepared.

| Analysis calculated for $C_{22}H_{24}O_5$ | | |
| --- | --- | --- |
| | C | H | N |
| Calc.: | 66.67 | 6.06 | 7.07 |
| Found: | 67.00 | 6.12 | 7.10 |

Step 2

500 mg of the product of Step 1 was dissolved in 35 ml of absolute ethanol and 50 mg of 10% palladium on carbon catalyst added. The suspension was hydrogenated at 50 psi until consumption of 2 mole equivalents of hydrogen occurred. The catalyst was removed by filtration and the title compound was isolated by vacuum distilation of the solvent (489 mg).

M.P.=173°

EXAMPLE 46

4-[1-(4-chlorobenzyl)-5-methoxy-3-methyl-1H-indol-2-yl]-2,2-dimethyl butanoic acid Following the method of Example 2, but using 1-[(4-chlorobenzyl)-1-(4-methoxyphenyl)]hydrazine hydrochloride and methyl 2,2-dimethyl-5-oxoheptanoate as starting materials, the title compound was prepared.

| Analysis calculated for $C_{23}H_{25}NO_3Cl$ | | | |
| --- | --- | --- | --- |
| | C | H | N |
| Calc.: | 69.28 | 6.52 | 3.51 |
| Found: | 69.21 | 6.93 | 3.22 |

EXAMPLE 47

4-[1-(4-chlorobenzyl)-5-fluoro-3-methyl-1H-indol-2-yl]-2,2-dimethyl butanoic acid Following the method of Example 2, but using 1-[4-chlorobenzyl]-1-[4-fluorophenyl]hydrazine hydrochloride and methyl-2,2-dimethyl-5-oxoheptanoate as starting materials, in t-butanol as solvent, the title compound was prepared.

| Analysis calculated for $C_{22}H_{23}NO_2ClF$ | | | |
|---|---|---|---|
| | C | H | N |
| Calc.: | 68.13 | 5.60 | 3.61 |
| Found: | 68.34 | 5.69 | 3.41 |

EXAMPLE 48

4-[1-(4-chlorobenzyl)-5-hydroxy-3-methyl-1H-indol-2-yl]-3-methyl butanoic acid

Following the method of Example 23, but using 4-[1-(4-chlorobenzyl)-5-methoxy-3-methyl-1H-indol-2-yl]-3-methyl butanoic acid as starting material, the title compound was prepared.

| Analysis calculated for $C_{21}H_{22}NO_3Cl$ | | | |
|---|---|---|---|
| C | H | N | |
| 67.13 | 5.92 | 3.76 | Calc. |
| 68.36 | 5.69 | 3.51 | Found |

EXAMPLE 49

4-[1-(4-methylthiobenzyl)-5-methoxy-3-methyl-1H-indol-2-yl]-3-methyl butanoic acid Following the method of Example 2, but using 1-[4-methylthiobenzyl]-1-[4-methoxyphenyl]hydrazine hydrochloride and methyl-3-methyl-5-oxoheptanoate as starting materials, in t-butanol as solvent, the title compound was prepared

| Analysis calculated for $C_{21}H_{27}NO_3S$ | | | |
|---|---|---|---|
| C | H | N | |
| 69.56 | 6.92 | 3.52 | Calc. |
| 69.85 | 7.20 | 3.50 | Found |

EXAMPLE 50

3-[1-(4-chlorobenzyl)-5-hydroxy-3-methyl-1H-indol-2-yl]-2,2-dimethyl propanoic acid Following the method of Example 23, but using 3-[1-(4-chlorobenzyl)-5-methoxy-3-methyl-1H-indol-2-yl]-2,2-dimethyl propanoic acid as starting material, the title compound was prepared.

M.P.=110° (decomposition)

EXAMPLE 51

3-[1-(4-chlorobenzyl)-5-hydroxy-3-methyl-1H-indol-2-yl]-3-methyl propanoic acid

Following the method of Example 23, but using 3-[1-(4-chlorobenzyl)-5-methoxy-3-methyl-1H-indol-2-yl]-3-methyl propanoic acid as starting material, the title compound was prepared.

| $C_{20}H_{20}NO_3Cl$ | | | |
|---|---|---|---|
| C | H | N | |
| 67.13 | 5.59 | 3.9 | Calc. |
| 67.22 | 5.74 | 3.97 | Found |

EXAMPLE 52

3-[1-(4-chlorobenzyl)-5-ethoxy-3-methyl-1H-indol-2-yl]-2,2-dimethyl propanoic acid The title compound of Example 50 was treated according to the method described in Example 39 using ethyl bromide as the alkylating agent. The product was isolated by chromatography on silica gel ($CH_2Cl_2$).

M.P.=148°

What is claimed is:

1. A compound of the Formula Ib:

wherein:
each $R^1$ is independently H or alkyl of 1 to 3 carbons;
$R^2$ is with the proviso that at least one of $R^1$ or $R^8$ is not H;
$R^3$ is alkyl of 1 to 6 carbons, but not cycloalkyl;
$R^4$ and $R^5$ is each independently:
 (1) hydrogen;
 (2) alkyl having 1 to 6 carbon atoms; or
 (3) M wherein M is
  a) halogen;
  b) $CF_3$;
  c) $SR^{12}$;
  d) $-SOR^{12}$;
  e) $-SO_2R^{12}$;
  f) $O-C(O)-R^{14}$; or
  g) CN;
$R^6$ and $R^7$ is each independently:
 (1) hydrogen;
 (2) alkyl having 1 to 6 carbon atoms; or
 (3) M wherein M is
  a) $OR^{12}$;
  b) halogen;
  c) $CF_3$;
  d) $SR^{12}$;
  e) $-SOR^{12}$;
  f) $-SO_2R^{12}$;
  g) $O-C(O)-R^{14}$; or
  h) CN;
each $R^8$ is independently H or alkyl of 1 to 4 carbons;
$R^9$ is COOH, $CH_2OH$, or CHO;
each $R^{12}$ is independently H, $C_1$ to $C_6$ alkyl, or benzyl;
each $R^{13}$ is independently H, phenyl, or $C_1$ to $C_6$ alkyl;

each $R^{14}$ is independently H, $C_1$ to $C_6$ alkyl, $CF_3$, or phenyl r and q is each independently 0 to 3;

p is 0 or 1;

p+q+r is 2-3;

or a pharmaceutically acceptable salt thereof.

2. A compound of claim 1 which is:

3-[1-(p-Chlorobenzyl)-5-chloro-3-methyl-2-indolyl]-propionic acid;

3-[1-(p-Chlorobenzyl)-3-methyl-5-fluoro-2-indolyl]-propionic acid;

3-[1-p-Chlorobenzyl-3-methyl-4,6-dichloro-2-indolyl]-propionic acid;

3-[1-p-Chlorobenzyl-3,4-dimethyl-2-indolylpropionic acid and 3-[1-(p-chlorobenzyl)-3,6-dimethyl-2-indolyl]propionic acid (as a mixture);

3-[1-p-Chlorobenzyl)-3,5-dimethyl-2-indolyl]-propionic acid;

3-[1-p-Chlorobenzyl)-3-methyl-2-indolyl]propionic acid;

3-[1-p-Chlorobenzyl)-5-bromo-3-methyl-2-indolyl]-propionic acid;

4-[1-(p-Chlorobenzyl)-3-methyl-5-fluoro-2-indolyl]-butanoic acid;

3-[1-p-Thiomethylbenzyl)-3-methyl-5-fluoro-2-indolyl]-propanoic acid;

3-[1-p-Methylsulfoxylbenzyl)-3-methyl-5-fluoro-2-indolyl]propanoic acid;

3-Methyl-4-[1-p-chlorobenzyl-5-fluoro-3-methylindol-2-yl]butanoic acid;

3-[1-p-Chlorobenzyl-5-acetoxy-3-methylindol-2-yl]-propionic acid;

3-[4,6-dichloro-1-(4-chlorobenzyl)-3-methyl-1H-indol-2-yl]propanoic acid;

3-[1-(4-chlorobenzyl)-3-methyl-5-fluoroindol-2-yl]-2,2-dimethyl propanoic acid;

3-[1-(4-chlorobenzyl)-3-methyl-5-fluoroindol-2-yl]-3-methyl-propanoic acid;

Methyl 4-[1-(4-chlorobenzyl)-3-methyl-5-fluoroindol-2-yl]-butanoate;

3-[1-(4-chlorobenzyl)-3-methyl-5-fluoroindol-2-yl]-2-methyl-butanoic acid;

3-[1-(4-chlorobenzyl)-3-methyl-5-chloroindol-2-yl]-2,2-dimethyl-propanoic acid;

4-[1-(4-chlorobenzyl)-5-fluoro-3-methyl-1H-indol-2-yl]-2,2-dimethyl butanoic acid;

4-[1-(4-chlorobenzyl)-5-fluoro-3-methyl-1H-indol-2-yl]-2,4,3,3-tetramethyl butanoic acid;

4-[1-(4-chlorobenzyl)-5-fluoro-3-methyl-1H-indol-2-yl]-4,3,3-trimethyl butanoic acid;

4-[1-(4-chlorobenzyl)-5-fluoro-3-methyl-1H-indol-2-yl]-2,2,3-trimethyl butanoic acid;

4-[1-(4-chlorobenzyl)-5-fluoro-3-methyl-1H-indol-2-yl]-2,3,3-trimethyl butanoic acid;

4-[1-(4-chlorobenzyl)-5-chloro-3-methyl-1H-indol-2-yl]-2,2,3-trimethyl butanoic acid;

4-[1-(4-chlorobenzyl)-3-methyl-5-trifluoromethyl-1H-indol-2-yl]-2,4,3,3-tetramethyl butanoic acid;

4-[1-(4-chlorobenzyl)-3-methyl-5-trifluoromethylthio-1H-indol-2-yl]-2,4,3,3-tetramethyl butanoic acid;

3-[1-(4-chlorobenzyl)-5-fluoro-3-methyl-1H-indol-2-yl]-2,2,3-trimethyl propanoic acid;

3-[1-(4-chlorobenzyl)-5-chloro-3-methyl-1H-indol-2-yl]-2,2,3-trimethyl propanoic acid;

3-[1-(4-chlorobenzyl)-3-methyl-5-fluoroindol-2-yl]-2,2-diethyl propanoic acid;

3-[1-(4-chlorobenzyl)-3-methyl-5-fluoroindol-2-yl]-2-ethyl propanoic acid; or

3-[1-(4-chlorobenzyl)-3-ethyl-5-fluoroindol-2-yl]-3-methyl propanoic acid.

3. A method of inhibiting leukotriene synthesis in a mammal, which comprises administering to a mammal an effective amount of a compound of claim 1.

4. A method of antagonizing prostaglandins in mammals, which comprises administering to a mammal an effective amount of a compound of claim 1.

5. A method of claim 4 wherein the prostaglandins are thromboxanes.

6. A pharmaceutical composition useful as a prostaglandin antagonist in mammals comprising a prostaglandin antagonizing amount of compound of claim 1.

* * * * *